(12) United States Patent
Delgadillo et al.

(10) Patent No.: US 12,076,021 B2
(45) Date of Patent: Sep. 3, 2024

(54) VASO-OCCLUSIVE DEVICES AND METHODS FOR MAKING AND USING SAME

(71) Applicants: STRYKER CORPORATION, Kalamazoo, MI (US); STRYKER EUROPEAN OPERATIONS LIMITED, Carrigtwohill (IE)

(72) Inventors: Jason Delgadillo, Kalamazoo, MA (US); Clifford Teoh, Los Altos, CA (US); Esther Koo, Kalamazoo, MA (US); Stella Than Chu, Kalamazoo, MA (US)

(73) Assignees: Stryker Corporation, Kalamazoo, MI (US); Stryker European Operations Limited, Carrigtwohill (IE)

( * ) Notice: Subject to any disclaimer, the term of this patent is extended or adjusted under 35 U.S.C. 154(b) by 0 days.

(21) Appl. No.: 18/336,011

(22) Filed: Jun. 15, 2023

(65) Prior Publication Data
US 2023/0329720 A1    Oct. 19, 2023

Related U.S. Application Data

(63) Continuation of application No. PCT/US2022/078932, filed on Oct. 28, 2022.
(Continued)

(51) Int. Cl.
*A61B 17/00* (2006.01)
*A61B 17/12* (2006.01)

(52) U.S. Cl.
CPC .. *A61B 17/12118* (2013.01); *A61B 17/12022* (2013.01); *A61B 17/12145* (2013.01);
(Continued)

(58) Field of Classification Search
CPC .................... A61B 17/12113; A61B 17/12172
See application file for complete search history.

(56) References Cited

U.S. PATENT DOCUMENTS

| 4,994,069 A |   | 2/1991 | Ritchart et al. |
| 5,649,949 A | * | 7/1997 | Wallace ............. A61B 17/1215 606/198 |

(Continued)

FOREIGN PATENT DOCUMENTS

JP          2003 230564        8/2003

OTHER PUBLICATIONS

PCT International Search Report and Written Opinion for PCT/US2022/078932, Applicant: Stryker Corporation, Form PCT/ISA/210, 220 and PCT/ISA/237, dated Feb. 8, 2023 (15 pages).

*Primary Examiner* — Michael J D'Abreu
(74) *Attorney, Agent, or Firm* — Vista IP Law Group, LLP

(57) ABSTRACT

A vaso-occlusive coil formed of a wire having a primary configuration in a constrained condition. The coil assumes a secondary configuration in a relaxed, unconstrained condition. The secondary configuration comprises a primary portion comprising a plurality of primary loops, including a distal-most primary loop. A distal anchoring loop is connected to the distal end of the distal-most primary loop. The distal anchoring loop has a substantially triangular shape and is much smaller than the distal-most primary loop. The distal anchoring loop prevents herniation of the device during deployment and retention within an anatomical cavity.

21 Claims, 18 Drawing Sheets

Related U.S. Application Data

(60) Provisional application No. 63/278,379, filed on Nov. 11, 2021.

(52) U.S. Cl.
CPC ............... *A61B 2017/00867* (2013.01); *A61B 2017/1205* (2013.01)

(56) References Cited

U.S. PATENT DOCUMENTS

| | | |
|---|---|---|
| 2015/0119920 A1 | 4/2015 | Mathis et al. |
| 2019/0015107 A1* | 1/2019 | Dias ................. A61B 17/12031 |
| 2019/0298387 A1 | 10/2019 | Qin et al. |

* cited by examiner

VASO-OCCLUSIVE DEVICES AND METHODS FOR MAKING AND USING SAME

RELATED APPLICATION DATA

This application is a continuation of International Patent Application No. PCT/US2022/078932, filed on Oct. 28, 2022, which claims priority to U.S. Provisional Patent Application No. 63/278,379, filed Nov. 11, 2021, the disclosures of all of which are hereby incorporated herein by reference in their entirety into the present application.

FIELD OF THE INVENTION

The present disclosure relates generally to medical devices and intravascular medical procedures and, more particularly, to devices for occluding vascular defects such as aneurysms, or other anatomical cavities, and methods for making and using such devices.

BACKGROUND

Vaso-occlusive devices or implants are used for a wide variety of reasons, including treatment of intra-vascular aneurysms. An aneurysm is a dilation of a vessel, such as a blood vessel, which may pose a risk to a patient's health due to rupture, clotting, or dissection. For example, rupture of an aneurysm in a patient's brain may cause a stroke, and lead to brain damage and death. Cerebral aneurysms may be detected in a patient, e.g., following seizure or hemorrhage, and may be treated by applying vaso-occlusive devices.

Commonly used vaso-occlusive devices include soft, helically wound coils formed by winding a platinum (or platinum alloy) wire strand about a "primary" mandrel. The coil is then wrapped around a larger, "secondary" mandrel, and heat treated to impart a secondary shape. For example, U.S. Pat. No. 4,994,069, issued to Ritchart et al., which is fully incorporated herein by reference as though set forth in full, describes a vaso-occlusive device that assumes a linear, helical primary shape when stretched for placement through the lumen of a delivery catheter, and a folded, convoluted secondary shape when released from the delivery catheter and deposited in the vasculature. In order to better frame and fill aneurysms, complex three-dimensional secondary shapes can be imparted on vaso-occlusive devices and the stiffness/flexibility of vaso-occlusive devices can be modified.

In order to deliver the vaso-occlusive devices to a desired site in the vasculature, e.g., within an aneurysmal sac, it is known to first position a small profile delivery catheter or "micro-catheter" at the site using a guidewire. Typically, the distal end of the micro-catheter is provided, either by the attending physician or by the manufacturer, with a selected pre-shaped bend, e.g., 45°, 26°, "J", "S", or other bending shape, depending on the particular anatomy of the patient, so that it will stay in a desired position for releasing one or more vaso-occlusive device(s) into the aneurysmal sac once the guidewire is withdrawn. A delivery or "pusher" assembly or "wire" is then passed through the micro-catheter until a vaso-occlusive device coupled to a distal end of the delivery assembly is extended out of the distal end opening of the micro-catheter and into the aneurysmal sac. Once in the aneurysmal sac, portions of the vaso-occlusive device may deform or bend to allow more efficient and complete packing. The vaso-occlusive device is then released or "detached" from the distal end of the delivery assembly, and the delivery assembly is withdrawn back through the micro-catheter. Depending on the particular needs of the patient, one or more additional vaso-occlusive devices may be pushed through the micro-catheter and released into the same aneurysmal sac.

Fluoroscopy is typically used to visualize vaso-occlusive devices during delivery into an aneurysm, while magnetic resonance imaging (MRI) is typically used to visualize the treatment site post-procedure (e.g., a few weeks after initial treatment of the aneurysm) to ensure that the aneurysmal sac is properly occluded. As such, it is important that vaso-occlusive devices be constructed in a manner that enables their radiopacity during treatment of the aneurysm, while minimizing any visualization obscuring artifacts created during the post-procedure MRI (i.e., being MRI-compatible). It is also preferable that such vaso-occlusive devices be "soft" (i.e., be laterally flexible or conformable), and thus atraumatic, to prevent rupturing of the delicate tissues of the aneurysm.

It is also important that such vaso-occlusive devices be chronically retained within the aneurysm. However, aneurysms with larger mouths, commonly known as "wide neck aneurysms," present difficulty in the placement and retention of vaso-occlusive devices within the aneurysm sacs, particularly with small and relatively thin vaso-occlusive coils which lack sufficient mechanical strength to maintain their position within such aneurysm sacs no matter how skillfully they are placed. For instance, small aneurysms (e.g., aneurysm having diameters less than about 7 mm or even smaller such as less than about 5 mm), often have the characteristics of a wide neck and a short dome. More specifically, small aneurysms often have relatively wide necks compared to the size of the aneurysm (i.e., the proportion of the width of the neck to the diameter of the aneurysm is often large for small aneurysms as compared to such proportion for larger aneurysms). Due to the relatively wide neck, small aneurysms (and wide neck aneurysms, in general) have greater risk of coil herniation into the parent vessel both during placement and retention. FIG. 1 shows a FIG. 1 depicts a portion of a vaso-occlusive coil herniating out of the aneurysm after introduction into the aneurysm.

Variations in the stiffness of the wire from which current vaso-occlusive devices are formed, and variations in the stiffness of the stretch resistant sutures often used in the current coil designs, also cause the oversizing of the leading (or distal) loop. The distal loop is the first loop of the vaso-occlusive device deployed into the aneurysm. The oversizing of the distal loop also causes a tendency for the distal tip (i.e., the leading end of the distal loop) to herniate out of the aneurysm during deployment. FIG. 1 shows one example of herniation during an initial deployment of a vaso-occlusive coil. As the vaso-occlusive coil is advanced out of the delivery catheter, the distal loop of the coil is unconstrained, and as the distal loop takes on its unconstrained configuration, the distal loop can bend around in the aneurysm such that the distal tip herniates out of the aneurysm and into the parent vessel. FIG. 2 shows another example in which the deployment of subsequent coils into the aneurysm causes significant displacement of the distal loop, causing rotation and tumbling of the distal loop which can also result in herniation due to this unpredictable movement. In order to compensate for these conditions, the clinician is forced to constantly manipulate the vaso-occlusive coil and/or delivery catheter, such as advancing, withdrawing and/or rotating the coil and catheter, as the coil is being deployed to prevent herniation.

Several placement techniques have also been developed to alleviate coil herniation during placement. One such placement technique, called a "remodeling or jailing technique," utilizes a balloon or stent deployed in the vessel adjacent to the neck region of the aneurysm to prevent the vaso-occlusive coils from exiting the aneurysmal sac. FIG. 3 depicts the remodeling technique using a balloon activated catheter. The balloon activated catheter is used to deploy a balloon adjacent to the neck region of the aneurysm. The balloon prevents coils from herniating from the aneurysm as the latter are implanted into the aneurysm. However, as depicted in FIG. 3, this technique creates a risk of the balloon pushing the tip of the catheter into the dome of the aneurysm and rupturing the aneurysm. FIG. 4 depicts a jailing technique using a stent. The stent is placed and expanded around the neck of the aneurysm to block the coils from exiting the aneurysm sac. Similar to the balloon activated catheter, the stent also risks the stent pushing the tip of the catheter into the dome of the aneurysm and rupturing the aneurysm. FIG. 5 depicts another placement technique for implanting a vaso-occlusive device called "recrossing." In this technique, the delivery catheter extends through an opening in the stent. The stent technique prevents the coils from herniating out of the aneurysm sac. However, due to inherent unpredictability of positioning the delivery catheter through an opening of the stent, there is a risk that manipulation of the delivery catheter to direct and position the delivery catheter can cause the catheter tip to push into the dome thereby rupturing the aneurysm.

To address these herniation and implantation issues, vaso-occlusive coils have been developed which provide more neck coverage and shape stability to effectively "frame" an aneurysm. However, the three-dimensional shapes of current vaso-occlusive devices are either not conducive to framing or are prone to herniation during deployment into an aneurysm. Small aneurysms are best treated with as few coils as possible and current vaso-occlusive devices are not able to balance shape stability and softness as a standalone unit. Indeed, the shapes and configuration of current vaso-occlusive devices result in a directly proportional relationship between shape stability and softness. In other words, the softer the device (i.e., the less resistant to deformation from an external force), the less stable the device, and vice versa (i.e., the less soft the device, the more stable the shape of the vaso-occlusive device). Hence, a softer coil is less likely to rupture an aneurysm but is not able to retain its shape such that it is more prone to herniation out of the aneurysm during deployment and/or retention. Conversely, a stiffer coil is better able to retain its shape and frame the aneurysm, but imparts higher stresses on the aneurysm wall, creating high risk of rupturing the aneurysm, especially small aneurysms with a high rupture risk. In addition, particularly with outward complex shapes employed by current designs, the initial distal loops (e.g., first and second loops) have a higher likelihood of herniating out of the aneurysm due to subsequent loops pushing them out during deployment.

Accordingly, there is a need for vaso-occlusive devices which can alleviate the issues of herniation during placement and retention and provide effective framing of the aneurysm, and at the same time have a sufficiently soft and pliable structure that will not rupture the aneurysm, especially small, wide-necked aneurysms.

SUMMARY

In accordance with one aspect of the presently disclosed medical devices and intravascular medical procedures, a vaso-occlusive device comprises an elongate vaso-occlusive device (e.g., from 0.5 to 100 cm in length) configured for implantation in an aneurysm sac. The vaso-occlusive devices disclosed herein are not limited to being configured and used for treating small, wide-necked aneurysms, but they are particularly well-suited for such configuration and use. Although the device disclosed herein are described as vaso-occlusive devices for occluding vascular cavities, such as aneurysms, the examples disclosed herein are not limited to being vaso-occlusive devices, but may be any medical device comprising the same or similar structure of the disclosed vaso-occlusive devices. For example, the medical device may be any suitable thrombectomy device, stent retriever, embolic filter, stent delivery system, other implantation device, guidewire, intravascular device, or other medical device.

The vaso-occlusive device typically has a delivery configuration (having a primary shape) when restrained within a delivery catheter and a deployed configuration (having a secondary shape different from the primary shape) when released from the delivery catheter into the aneurysmal sac.

The vaso-occlusive device includes a primary coil, formed of a wire, having a primary configuration in a constrained condition. For instance, the primary configuration may be a shape of the coil when it is constrained within a delivery catheter, such as a helical coil shape, linear shape, or the like. The vaso-occlusive device is also configured to assume a secondary configuration in a relaxed, unconstrained condition, such as when the coil is released from a delivery catheter with no external forces exerting on the coil.

The secondary configuration of the vaso-occlusive device comprises a plurality of primary loops, and a distal anchoring loop which is specifically sized and shaped to minimize the risk of herniation during deployment and also to facilitate chronic retention after placement in an aneurysm. The primary loops include a distal primary loop which is the distal-most loop of the primary loops. The distal primary loop has a proximal end and a distal end. The proximal end is connected to the other primary loops, and the distal end is connected to the distal anchoring loop. Each of the individual loops of the distal primary loop lies substantially in a first plane and planes parallel to the first plane, such that each of the individual loops lies in a respective substantially two-dimensional surface. The distal primary loop has a perimeter which is the length of the wire forming the distal primary loop from the proximal end to the distal end of the primary loop. The distal primary loop typically has a substantially circular, or substantially circular arc, shape. As used herein, the term "substantially circular shape" or "substantially circular arc shape" means a shape which is primarily circular.

The distal anchoring loop is typically at the distal-most end of the vaso-occlusive device such that it is the first element of the vaso-occlusive device to be inserted into the aneurysm during deployment of the vaso-occlusive device. The distal anchoring loop has a substantially triangular shape and is substantially smaller in size than the distal primary loop. As used herein, the term "substantially triangular shape" means a shape having three distinct sides joined at three vertices, wherein the vertices may be sharp corners or arcs forming filleted vertices joining the sides. The distal anchoring loop has an overall length which is the length of the wire forming the distal anchoring loop. In other words, the length of the 3 sides of the substantially triangular shape, and the length(s) of any arcs forming the filleted vertices of the substantially triangular shape. In one aspect, the distal anchoring loop has an overall length of 25% to 75% of the perimeter of the distal primary loop. In an alternative aspect of the vaso-occlusive device, the distal anchoring loop may have an overall length of 40% to 60% of the perimeter of the distal primary loop. In still another alternative aspect of the vaso-occlusive device, the distal anchoring loop may have an overall length of less than 60% of the perimeter of the distal primary loop.

The distal anchoring loop is positioned within a projection of the distal primary loop. In other words, the distal anchoring loop is positioned either within the perimeter of the distal primary loop (e.g., co-planar), or it is positioned within a perpendicular projection of the perimeter of the distal primary loop (e.g., the distal anchoring loop may be parallel to the first plane and out of each of the planes of the distal primary loop).

In another aspect of the vaso-occlusive device, the secondary configuration may also include a body portion proximal of the primary portion. The body portion may comprise a coil formed from the wire and extending proximal from the primary portion. For instance, the body portion may be a helical coil or other suitable shape for filling the aneurysm.

In another aspect, the substantially triangular shape of the distal anchoring loop may formed of a base and two sides connected to the base, wherein each of the sides is connected to the base by rounded vertices, and the angle between the base and each of the sides is from 15° to 75°. Alternatively, the angle between the base and each of the sides may be from 25° to 50°.

In yet another aspect, a starting point of the distal anchoring loop where the distal anchoring loops connects to the distal primary loop is between a 10:00 o'clock position and an 11:00 o'clock position relative to a longitudinal axis of the primary configuration of the coil being at a 12:00 o'clock position. This feature provides improved stability and avoidance of herniation out of the aneurysm during deployment and retention.

In another aspect, the distal anchoring loop may be connected to the distal primary loop via a transition segment. Accordingly, the starting point of the distal anchoring loop is where the distal anchoring loop connects to the transition segment. The transition segment can be used to position the distal anchoring loop out of the planes of the distal primary loop, as described herein.

In still another aspect of the vaso-occlusive device, the distal anchoring loop may lie out of the planes of the distal primary loop. For instance, the distal anchoring loop may be parallel to the first plane, and displaced outwardly relative to an interior of the vaso-occlusive device from all of the planes of the individual loops of the distal primary loop.

In yet another aspect, the vaso-occlusive device may further comprise a second distal anchoring loop which is distal of the distal anchoring loop. The second distal anchoring loop having may have substantially the same shape and size as the distal anchoring loop may be and positioned parallel to the distal anchoring loop.

In another feature of the vaso-occlusive device, the primary configuration may comprise an elongate helical coil. This primary configuration provides good flexibility for the vaso-occlusive device and a relatively compact form during deployment in a delivery catheter, while also providing sufficient stiffness for pushing the device out of the delivery catheter.

In yet another aspect, the wire may be formed from a shape memory material. In this way, the secondary configuration may be set by winding the wire on a mandrel and heat treating the wire wound on the mandrel.

In another feature of the vaso-occlusive device, each of the primary loops may have an average outer diameter between 10 to 90 percent of a diameter of an aneurysm the vaso-occlusive device is designed to treat. Alternatively, each of the primary loops may have an average outer diameter between 55 to 85 percent of a diameter of an aneurysm the vaso-occlusive device is designed to treat. These sizing constraints of the primary loops provides good framing of the aneurysm, and provides shape stability to the vaso-occlusive device upon deployment.

In additional aspects of the vaso-occlusive device, the primary portion may comprise a pyramidal portion formed from the primary loops, wherein each of the primary loops comprises a winding of the wire forming a closed loop of greater than 360°, and the plurality of primary loops are arranged in a pyramidal shape such that each primary loop lies in a different lateral face of the pyramidal shape. This secondary configuration provides a balanced solution between shape stability and softness such that the vaso-occlusive device has a stable shape which prevents herniation during deployment and retention and provides effective framing of the aneurysm, while also having sufficient softness/pliability to avoid rupturing the aneurysm. The pyramidal shape has an inherent ability to effectively dissipate forces applied to its apexes, thereby reducing the risk of imparting excessive forces on the walls of the aneurysm which could rupture the aneurysm.

In still another aspect, the primary loops may be tapered to provide inward facing loops. Each of the primary loops has a perimeter which tapers outwardly from an interior of the pyramidal portion. Due to the outwardly tapering diameter, the loops or turns of each of the distal coils are inward facing. In other words, the surface of the loops faces inward toward the geometric interior of the pyramidal shape of the pyramidal portion. For example, for a helical coil shaped primary loop, the diameter of the loops taper outwardly such that the interior part of the loops of the coil has a smaller diameter than the outer part of the loops of the coil. The inward facing loops tend to avoid herniating out of the aneurysm during deployment and retention, and the pyramidal configuration of the distal coils also provides shape stability which effectively frames the aneurysm while also exhibiting a soft and pliable structure which avoids imparting excessive forces on the walls which could rupture the aneurysm. In still another aspect, each of the primary loops may be connected to the adjacent primary loop(s) by a transition segment of the wire between each primary loop and the adjacent primary loop(s).

In still another aspect, the secondary configuration may also have a body portion proximal of the pyramidal portion. The body portion may comprise a coil formed from the wire and extending proximal from the primary portion. For instance, the body portion may be a helical coil or other suitable shape for filling the aneurysm.

In still another aspect, each of the primary loops may comprise at least 1⅓ loops or turns (winding of 480°), or from 1⅔ loops to 2⅔ loops (winding of 960°). In still another feature, the primary loops may be overlapping in the transition from one primary loop to an adjacent primary loop. In other words, the transition segment overlaps the coil as it extends from one distal coil to a subsequent, adjacent coil.

Methods of making any of the vaso-occlusive devices described herein, and mandrels used to make the vaso-occlusive devices, are also disclosed. In one method of making a vaso-occlusive device using a mandrel, a mandrel for forming the vaso-occlusive device is provided. The mandrel comprises support member and a plurality of primary loop posts extending from the support member and spaced around the support member. The primary loop posts include a distal primary loop post having a first end connected to the support member and a second end extended away from the support member. The distal primary loop post has a first perimeter for winding the wire onto the distal primary loop post. The mandrel also has a distal anchoring loop sub-mandrel coupled to the second end of the distal primary loop post. The distal anchoring loop sub-mandrel is configured to form a substantially triangular shaped loop from a wire wound around the distal anchoring loop sub-mandrel.

A coil formed of wire having a primary configuration is then wound around the mandrel. The wire is wound around each of the primary loop posts to form a primary portion of the vaso-occlusive device comprising a plurality of primary loops, including a distal primary loop formed by winding the wire around the distal primary loop post. The distal primary loop is the distal-most primary loop of the vaso-occlusive device and has a proximal end, a distal end and a perimeter length from the proximal end to the distal end. The wire is also wound around the distal anchoring loop sub-mandrel to form a distal anchoring loop connected to the distal end of the distal primary loop. The distal anchoring loop has a substantially triangular shape having an overall length of 25% to 75% of the perimeter length of the distal primary loop. The distal anchoring loop is positioned within a projection of the distal primary loop.

In another aspect of the method of making a vaso-occlusive device, the mandrel further comprises a body post extending from the support member. The method further comprises winding the wire around the body post forming a body portion of the vaso-occlusive device proximal of the primary portion. The body portion may comprise a helical coil extending proximally from the primary portion.

In another aspect of the method, the primary portion may comprise a pyramidal portion formed from the primary loops. Each primary loop post has a longitudinal axis which is oriented such that respective planes perpendicular to each respective longitudinal axis have an intersection which forms a pyramidal shape having an apex distal to the distal coil posts. Upon winding the wire around each of the primary loop posts to form a closed loop of greater than 360°, and the resulting plurality of primary loops are arranged in a pyramidal shape such that each primary loop lies in a different lateral face of the pyramidal shape.

In still another aspect of the method, the support member may be a central, spherical element and in winding the wire around the mandrel, a transition segment between adjacent primary loops is formed by traversing the wire along the spherical element.

In yet another aspect of the method, each of the primary loop posts may have a cross-sectional diameter which tapers outwardly as the primary loop post extends away from the spherical element. Hence, each of the primary loops has a perimeter which tapers outwardly from an interior of the primary portion (which in some cases is pyramidal).

In another aspect of the method, the pyramidal shape is a polyhedral shape formed of a polygonal base having n number of sides and n number of lateral faces connecting to an apex.

In another aspect of the method, the substantially triangular shape of the distal anchoring loop is formed of a base and two sides connected to the base, wherein each of the sides is connected to the base by rounded vertices, and the angle between the base and each of the sides is from 15° to 75°. Alternatively, the angle between the base and each of the sides may be from 25° to 50°.

In still another aspect of the method, the overall length of the distal anchoring loop is from 40% to 60% of the perimeter of the distal primary loop. In another feature of the method, the starting point of the distal anchoring loop where the distal anchoring loops connects to the distal primary loop is between a 10:00 o'clock position and an 11:00 o'clock position relative to a longitudinal axis of the primary configuration of the coil being at a 12:00 o'clock position.

In another aspect of the method, the distal anchoring loop may be connected to the distal primary loop via a transition segment, such that the starting point of the distal anchoring loop is where the distal anchoring loop connects to the transition segment.

In still another aspect of the method, the distal anchoring loop may lie out of the planes of the distal primary loop. For example, the distal anchoring loop may be parallel to the first plane, and displaced outwardly relative to an interior of the vaso-occlusive device from all of the planes of the distal primary loop.

In another feature of the method, the primary configuration is a configuration of the coil in a constrained condition and the primary configuration comprises an elongate helical coil.

In still another feature of the method, the wire may be formed from a shape memory material. The method further include heat treating the wire wound around the mandrel to set the secondary configuration of the vaso-occlusive device. In another aspect, the secondary configuration is a relaxed, unconstrained configuration of the coil.

In still other aspects of the method, of the primary loops may have an average outer diameter between 10 to 90 percent of a diameter of an aneurysm the vaso-occlusive device is designed to treat. Alternatively, each of the primary loops may have an average outer diameter between 55 to 85 percent of a diameter of an aneurysm the vaso-occlusive device is designed to treat.

In still another aspect of the method, the vaso-occlusive device can be wound in the opposite direction. In other words, the wire is first wound around the body post to form the body portion. Then the wire is wound around each of the primary loop posts to form to form a respective closed loop of greater than 360°, and the resulting plurality of primary loops are arranged in a pyramidal shape such that each primary loop lies in a different lateral face of the pyramidal shape. The wire is then wound around the distal anchoring post to form the distal anchoring loop. The method may include any of the other features and aspects as described herein. Indeed, the steps of the method for forming the vaso-occlusive device may be performed in any suitable order.

In additional aspects of the method of making a vaso-occlusive device, the vaso-occlusive device may have any one or more of the aspects and features disclosed herein.

In additional aspects of the devices disclosed herein, the vaso-occlusive devices disclosed herein may be a part of a vaso-occlusive system comprising a vaso-occlusive assembly and a delivery assembly. For example, a vaso-occlusive assembly may comprise any of the vaso-occlusive devices described herein, and a pusher member detachably coupled to a proximal end of the vaso-occlusive device. The pusher member is configured to allow a clinician to advance the vaso-occlusive device along a delivery catheter through a patient's vasculature to a target site, such as an aneurysm being treated with the vaso-occlusive device, and to push the vaso-occlusive device out of the distal end of the delivery catheter to deploy the vaso-occlusive device.

In still another aspect, the vaso-occlusive assembly may also include a detachment device detachably coupling the pusher member to the vaso-occlusive device. For example, the detachment device may comprise an electrolytic detachment, mechanical connector, heat activated detachment, dissolving detachment, etc. The delivery assembly may include a delivery catheter into which the vaso-occlusive device may be installed in its compact, delivery configuration. The delivery assembly may also include a guidewire for guiding the delivery catheter to a target implantation site within a patient's vasculature, such as an aneurysm. The guidewire is then be removed, and the vaso-occlusive device is advanced through the delivery catheter to the target implantation site.

Methods of using any of the vaso-occlusive devices, or other medical devices described herein are also disclosed. In one method, the vaso-occlusive device is inserted into, and advanced through a delivery catheter device in its primary configuration, which is a compact, delivery configuration. The delivery catheter is first inserted into the patient's vasculature and is advanced within the vasculature to position the distal end of the delivery catheter at the target anatomical cavity, such as an aneurysm in this example. It is understood that the target anatomical cavity may be any suitable anatomical site within the vasculature into which the vaso-occlusive device is being deployed. If a guidewire is utilized, the guidewire is first inserted into the patient's vasculature and advanced through the vasculature to the site of the aneurysm. Then, the delivery catheter is advanced along the guidewire to the aneurysm, and then the guidewire is removed.

The vaso-occlusive device is then inserted in its primary configuration into the delivery catheter and advanced along the delivery catheter to the target anatomical cavity. The vaso-occlusive device is then pushed distally out of the delivery catheter, such as by using a pusher-member. As the vaso-occlusive device is advanced out of the delivery catheter, the distal anchoring loop is the first structure of the vaso-occlusive device to be inserted into the target anatomical cavity. As the distal anchoring loop exits the delivery catheter and enters the cavity, the distal anchoring loop assumes its secondary configuration comprising a substantially triangular shape. As the vaso-occlusive device continues to be extruded from the delivery catheter, the distal primary loop enters the cavity. The size and shape of the distal anchoring loop maintains or "anchors" the vaso-occlusive device into the cavity as the device is deployed into the target anatomical cavity, thereby preventing herniation with no, or minimal, manipulation required by the clinician. As the vaso-occlusive device continues to be released from the delivery catheter and inserted into the cavity, each of the primary loops inserts into the cavity and expands toward the respective secondary configuration thereby effectively framing and filling the cavity with a stable, yet flexible structure which avoids damaging or rupturing the cavity tissue, while also providing excellent retention within the cavity. Once the entire vaso-occlusive device is inserted into the aneurysmal sac, the vaso-occlusive device may be detached from the pusher-member, such as by actuating or activating the detachment device.

In some cases, a single vaso-occlusive device may be sufficient to fill and occlude the aneurysm. If multiple vaso-occlusive devices are needed, this process may be repeated to deliver a sufficient number of vaso-occlusive devices to fill and occlude the aneurysm.

Accordingly, there is a need for vaso-occlusive devices which can alleviate the issues of herniation during placement and retention and provide effective framing of the aneurysm, and at the same time have a sufficiently soft and pliable structure that will not rupture the aneurysm, especially small, wide-necked aneurysms.

Other and further aspects and features of embodiments of the disclosed inventions will become apparent from the ensuing detailed description in view of the accompanying figures.

BRIEF DESCRIPTION OF THE DRAWINGS

The drawings illustrate the design and utility of various aspects of the devices and methods disclosed herein, in which similar elements are referred to by common reference numerals. It should be noted that the figures are not drawn to scale and that elements of similar structures or functions are represented by like reference numerals throughout the figures. It should also be noted that the figures are only intended to facilitate the description of the various aspects of the disclosed technology. They are not intended as an exhaustive description of the technology or as a limitation on the scope of the technology, which is defined only by the appended claims and their equivalents. In addition, an illustrated example of the disclosed technology need not have all the aspects or advantages shown or described herein. An aspect or an advantage described in conjunction with a particular example of the disclosed technology is not necessarily limited to that example and can be practiced in any other examples even if not so illustrated. In order to better appreciate how the above-recited and other advantages and objects of the present technology are obtained, a more particular description of the present technology briefly described above will be rendered by reference to specific examples thereof, which are illustrated in the accompanying drawings. With the understanding that these drawings and corresponding description depict only illustrative examples of the disclosed technology and are not therefore to be considered limiting of its scope, the technology will be described and explained with additional specificity and detail through the use of the accompanying drawings in which:

DETAILED DESCRIPTION

Figure 1:
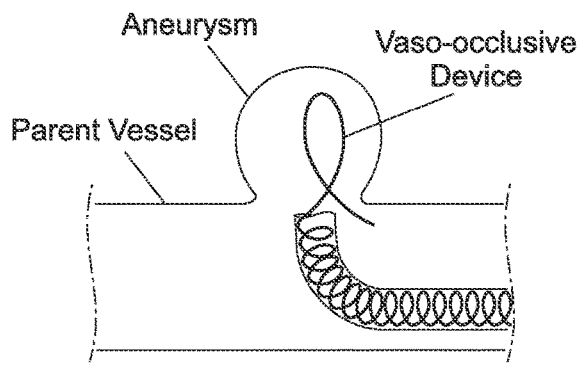
FIG. 1 is a side, cross-sectional view of a delivery catheter deploying a vaso-occlusive device in which the vaso-occlusive device is herniating upon deployment of the distal most loop.
Figure 2:
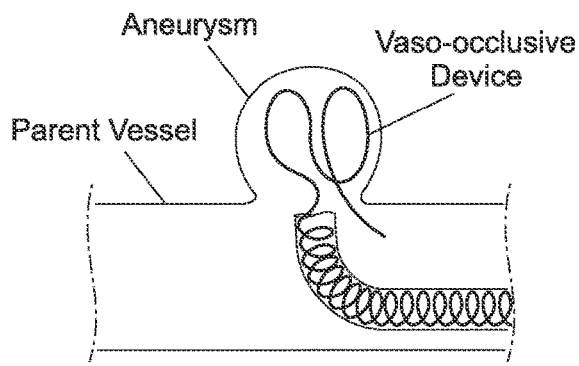
FIG. 2 is a FIG. 1 is a side, cross-sectional view of a delivery catheter deploying a vaso-occlusive device in which the vaso-occlusive device is herniating upon deployment of a loop subsequent to deployment of a distal most loop.
Figure 3:
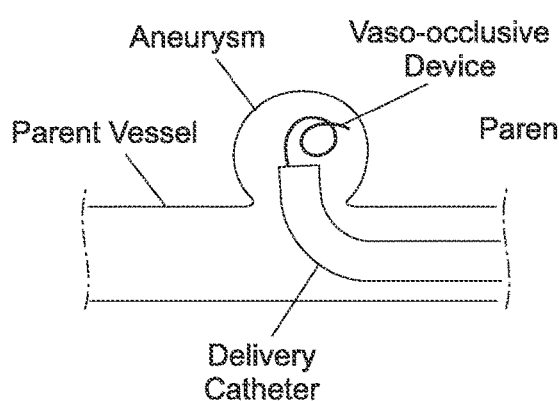
FIG. 3 is cross-sectional, side view of a delivery catheter deploying a vaso-occlusive device and a balloon activated catheter used in a remodeling or jailing technique.
Figure 3:
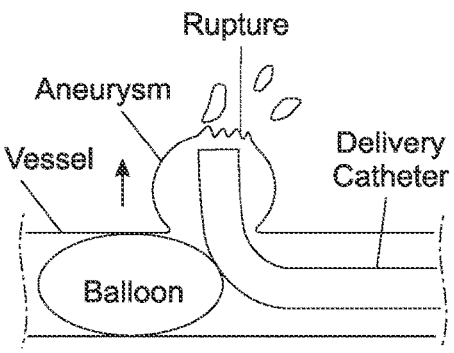
Figure 4:
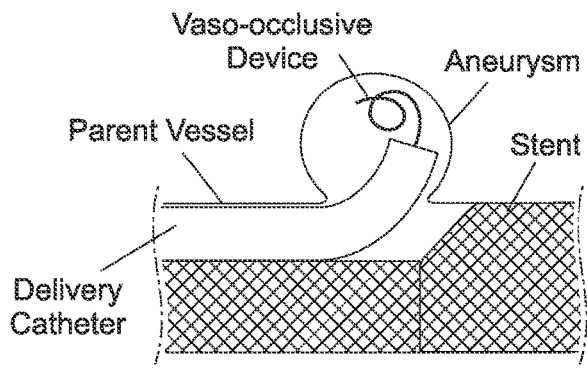
FIG. 4 is a cross-sectional, side view of a delivery catheter deploying a vaso-occlusive device and a stent used in a jailing technique.
Figure 4:
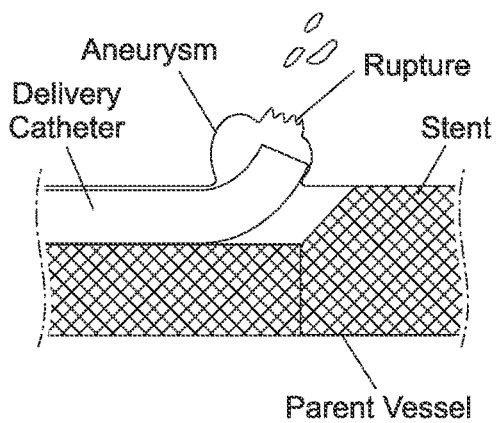
Figure 5:
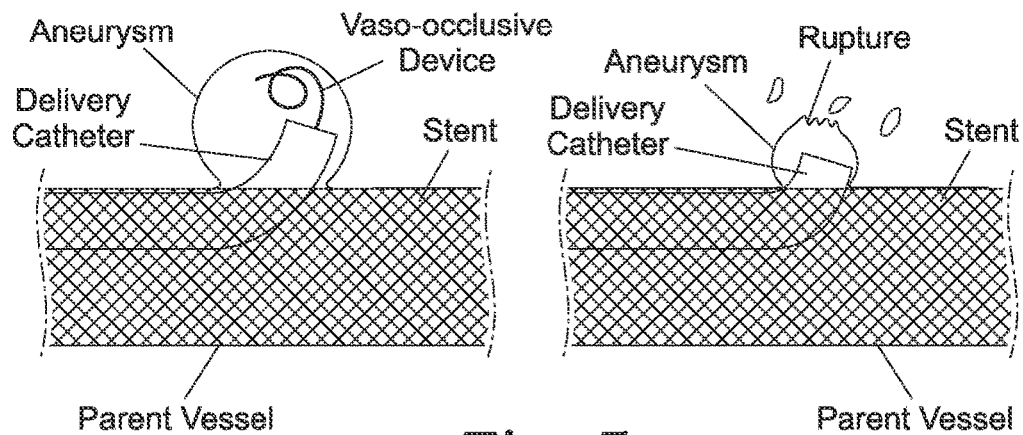
FIG. 5 is a cross-sectional, side view of a delivery catheter deploying a vaso-occlusive device and a stent used in a recrossing technique.
Figure 6:
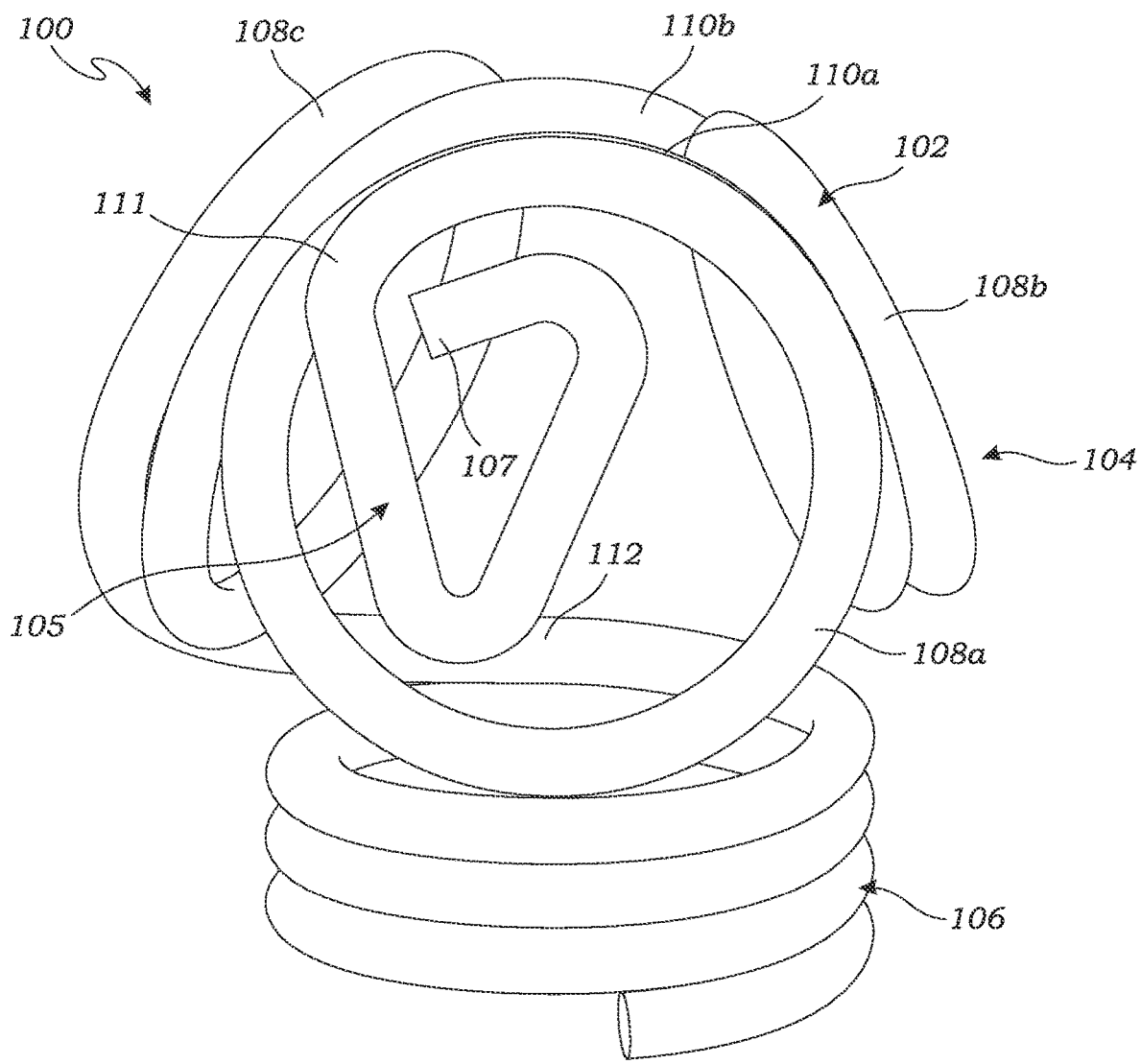
FIG. 6 is a side, perspective view of a vaso-occlusive device as disclosed herein, in a relaxed, deployed configuration.

Referring to FIG. 6, an example of a vaso-occlusive device 100, as disclosed herein, is illustrated. The examples of vaso-occlusive devices are described in detail herein as vaso-occlusive devices for occluding aneurysms, with the understanding that the devices are not limited to being configured for deployment into an aneurysm, but may be sized and configured for occluding any suitable anatomical cavity. Moreover, the devices are not limited to being occlusive devices, but may be any suitable medical device, such as a thrombectomy device, stent retriever, embolic filter, stent delivery system, other implantation device, guidewire, intravascular device, or the like.

FIG. 6 depicts the vaso-occlusive device 100 in its secondary configuration in a relaxed, unconstrained condition. In other words, FIG. 6 shows the vaso-occlusive device 100 when there are no external forces exerting on the vaso-occlusive device 100. The secondary configuration of the vaso-occlusive device 100 has a primary portion 104, a base portion 106, and a distal anchoring loop 105. The primary portion 104 is distal to the body portion 106, and the distal anchoring loop 105 is distal to the primary portion 104. The terms "distal" and "proximal" as used herein are relative to the vaso-occlusive device 100 as it is intended to be deployed, wherein the term "distal" refers to being situated toward the end of the device 100 which is inserted first, and "proximal" refers to being situated toward the end of the device 100 which is inserted last.

The vaso-occlusive 100 comprises a coil formed of a wire 102 having a primary configuration in a constrained configuration. For instance, the constrained configuration may be an elongate, helical coil when the wire 102 is constrained within a delivery catheter (see FIG. 20A). Typically, the primary shape has a longitudinal length between 1 cm to 70 cm. The wire 102 is made from any suitable material, but typically comprises a radiopaque, shape memory material, such as the platinum group metals, including platinum, rhodium, palladium, and rhenium, as well as tungsten, gold, silver, tantalum, and alloys of these metals.

Figure 20A:
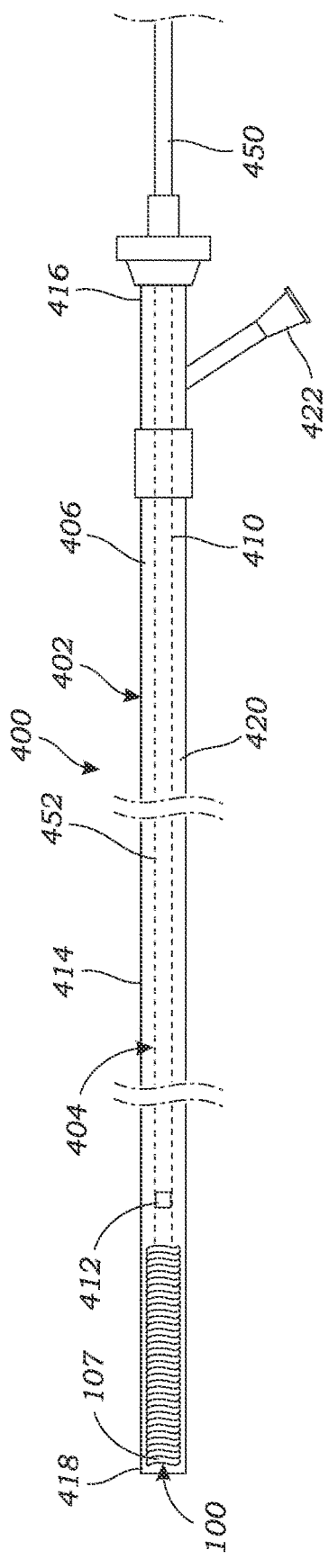
FIG. 20A is a cross-sectional side view of a vaso-occlusive system including the vaso-occlusive device of FIG. 6 in its restrained, delivery configuration within a delivery catheter.

The distal anchoring loop 105 in the secondary configuration of the vaso-occlusive device 100 is formed by a distal-most portion of the vaso-occlusive device 100 in its primary configuration (see FIG. 20A). The primary portion 104 in the secondary configuration of the vaso-occlusive device 100 is formed by a portion of the vaso-occlusive device 100 in its primary configuration just proximal of the distal anchoring loop (see FIG. 20A).

The primary portion 104 includes a plurality of primary loops 108 wound from the wire 102. In the illustrated example of FIG. 6, the primary portion 104 includes three primary loops 108a, 108b, and 108c. The first primary loop 108a (also referred to as the "distal primary loop") is the distal-most primary loop 108, the second primary loop 108b is just proximal of the first primary loop 108a, and the third primary loop 108c is just proximal of the second primary loop 108b (i.e., it is the proximal-most primary loop 108). The primary loops 108 are connected end to end, such that a proximal end of the first primary loop 108a is connected to the distal end of the second primary loop 108b, and the proximal end of the second primary loop 108b is connected to the distal end of the third primary loop 108c.

Figure 7:
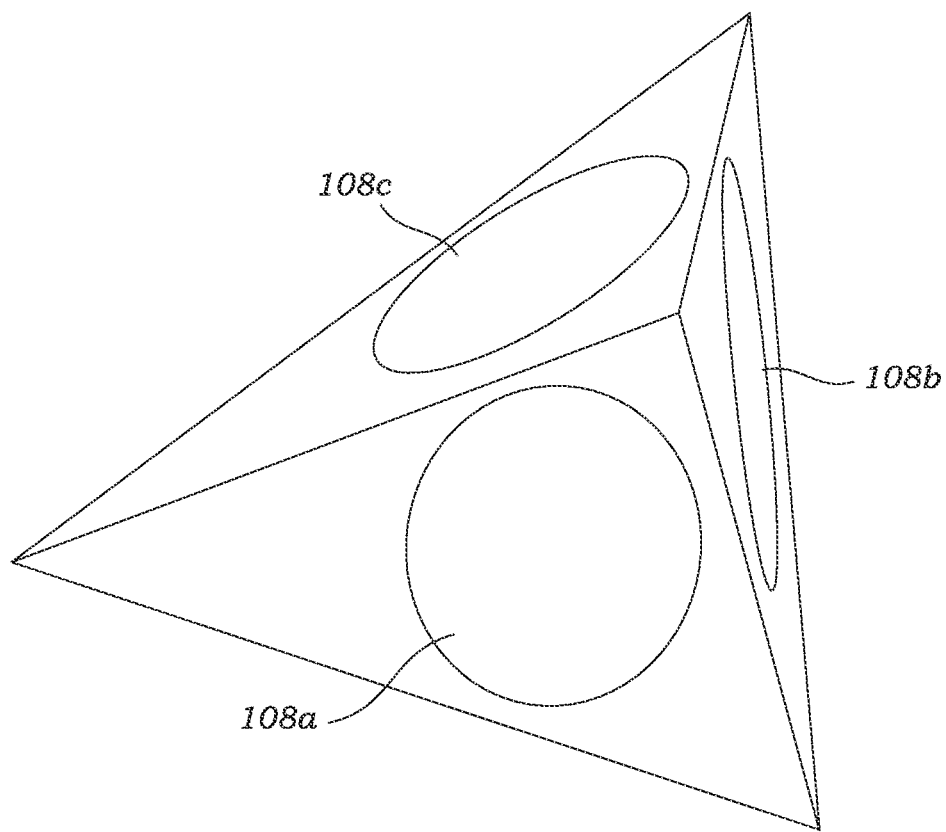
FIG. 7 is a top perspective view of a simplification of the intersecting planes of the 3 distal coils of FIG. 6 forming the pyramidal portion of the vaso-occlusive device in the shape of a triangular pyramid.

In the illustrated example of FIG. 6, the primary portion 104 includes three primary loops 108a, 108b, and 108c, arranged to form a pyramidal shape having three lateral faces, also referred to as a triangular pyramid. The pyramidal shape in the example of FIG. 6 is referred to as a triangular pyramid because the base of the pyramidal shape (the primary loops 108 do not include a distal coil at the base of the pyramidal shape, however, the body portion 106 described below may form the base portion of the pyramidal shape) is a triangle, wherein a respective coil 108 lies in each lateral face of the triangular pyramid. The respective planes in which the respective turns/loops of each primary loop 108 lie are non-parallel and intersect with each other. As depicted in FIG. 6, a simplification of the intersecting planes of the primary loops 108 forms a tetrahedral, more specifically, a triangular pyramid. The vaso-occlusive device 100 of FIG. 6 is an example, and is not limited to primary loops 108 forming a triangular pyramid shape, but may be other suitable pyramidal shapes, such as n number of primary loops 108 forming a pyramid having a polygonal base having n number of sides and n number of lateral faces connecting to an apex. For instance, the vaso-occlusive device 100 may have primary loops 108 in each lateral face of a pyramidal shape which may be a square pyramid having a square base and 4 lateral faces, a quadrilateral pyramid having a quadrilateral base and 4 lateral faces, a pentagonal pyramid having a pentagonal base and 5 lateral faces, etc. As depicted in FIG. 7, the primary portion 104 may have 4 primary loops 108 in each lateral face arranged to form a square pyramid having a square base and 4 lateral faces.

Turning back to FIG. 6, each primary loop 108 includes a winding forming a closed loop of greater than 360°, i.e., at least a complete, closed loop. In the illustrated vaso-occlusive device 100, each primary loop 108 includes a winding of 1⅓ loops (also referred to as "turns"), which is equivalent to a winding of 480°. Alternatively, each primary loop 108 may have at least 1⅓ turns, or between 1⅓ turns (480°) and 2⅔ turns (960°).

Figure 8:
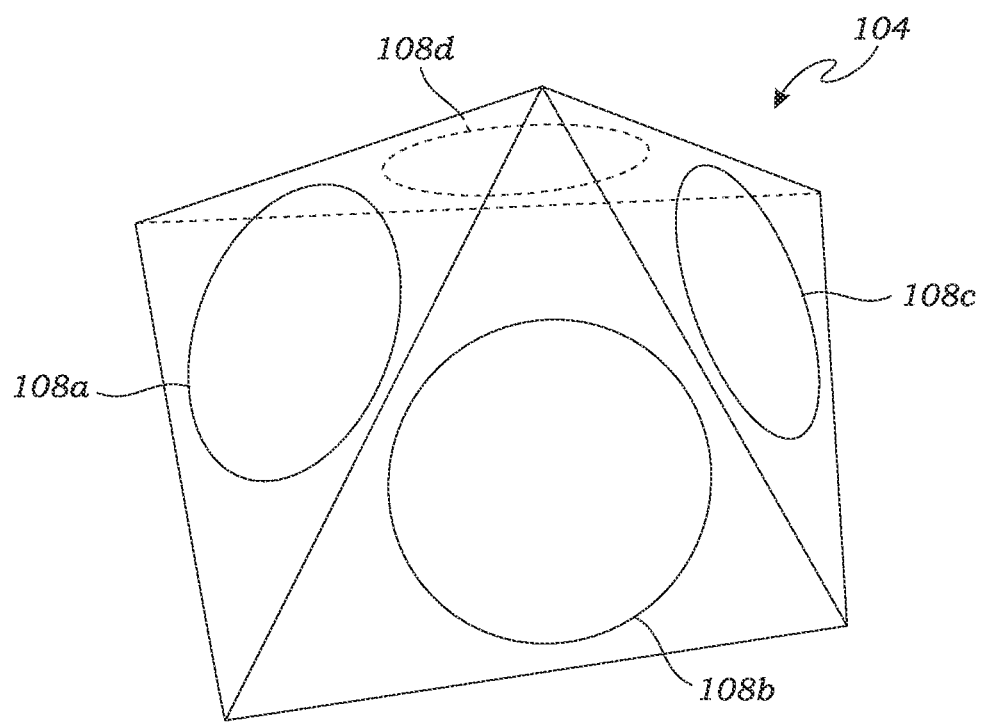
FIG. 8 is a top perspective view of a simplification of the intersecting planes of 4 distal coils forming the pyramidal portion of a vaso-occlusive device in the shape of a square pyramid.
Figure 9:
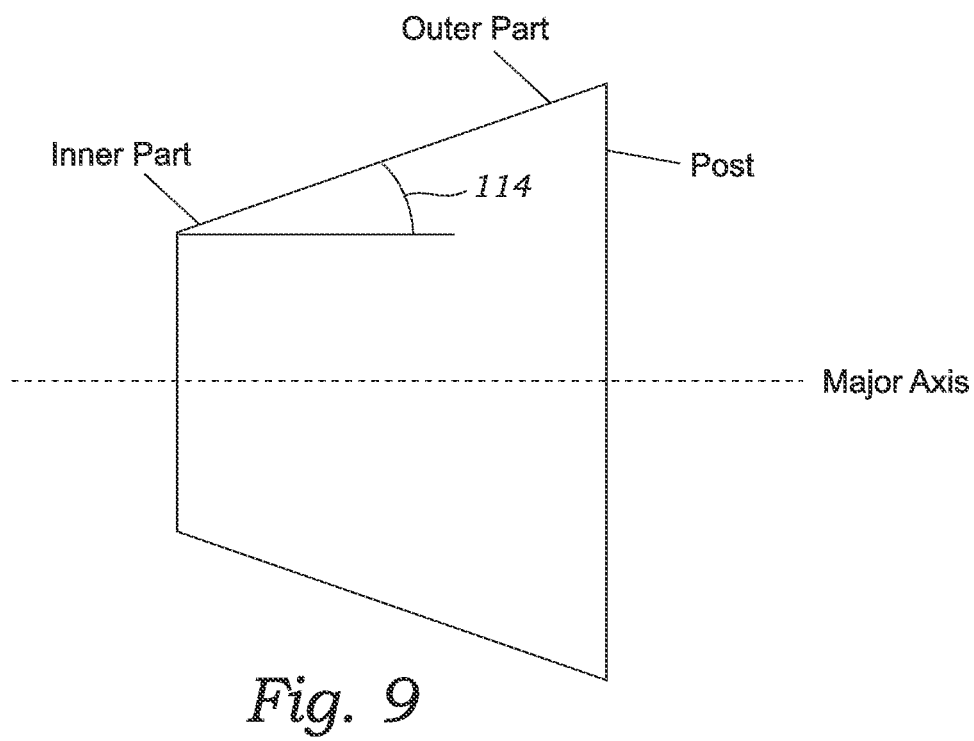
FIG. 9 is a side view of primary loop post for forming the primary loops of a vaso-occlusive device illustrating the taper angle for the primary loops.

The winding of each of the primary loops 108 may also have a width which tapers outwardly from a reference point of the interior of the primary portion 104. In the case of a helical coil as depicted in the example of FIG. 6, the width of each primary loop 108 is the diameter of the coil. If the primary loops 108 are wound in a different shape, such as a square, pentagon, or other polygonal or curved shape, the width may be an average width, such an average of the maximum and minimum width drawn through the geometric center of the shape. Turning to the example of FIG. 6, the diameter of each primary loop 108 tapers such that the diameter of the outer part of the coil 108 is larger than the diameter of the inner part of the coil 108. This may be better explained with reference to a cross-section of a cylindrical post upon which the primary loop 108 are wound, as shown in FIG. 9. The post has a diameter which tapers outwardly from the inner part of the post to the outer part of the post, as depicted in FIG. 8. The angle 114 of the post taper defines the angle of the taper of the primary loop 108 in the secondary configuration of the vaso-occlusive device 100. Due to the outwardly tapering diameter, the loops or turns of each of the primary loops 108 is inward facing. In other words, the surface of the loops faces inward toward the geometric interior of the pyramidal shape of the primary portion 104.

Each of the primary loops 108 has a diameter (defined as the diameter of the inner most loop of each primary loop 108) between 10 to 90 percent of a diameter of an aneurysm (or other anatomical cavity to be filled by the vaso-occlusive device 100) the vaso-occlusive device 100 is designed to treat. Alternatively, the diameter of each primary loop 108 may be between 55 to 85 percent of a diameter of an aneurysm the vaso-occlusive device 100 is designed to treat.

Figure 10:
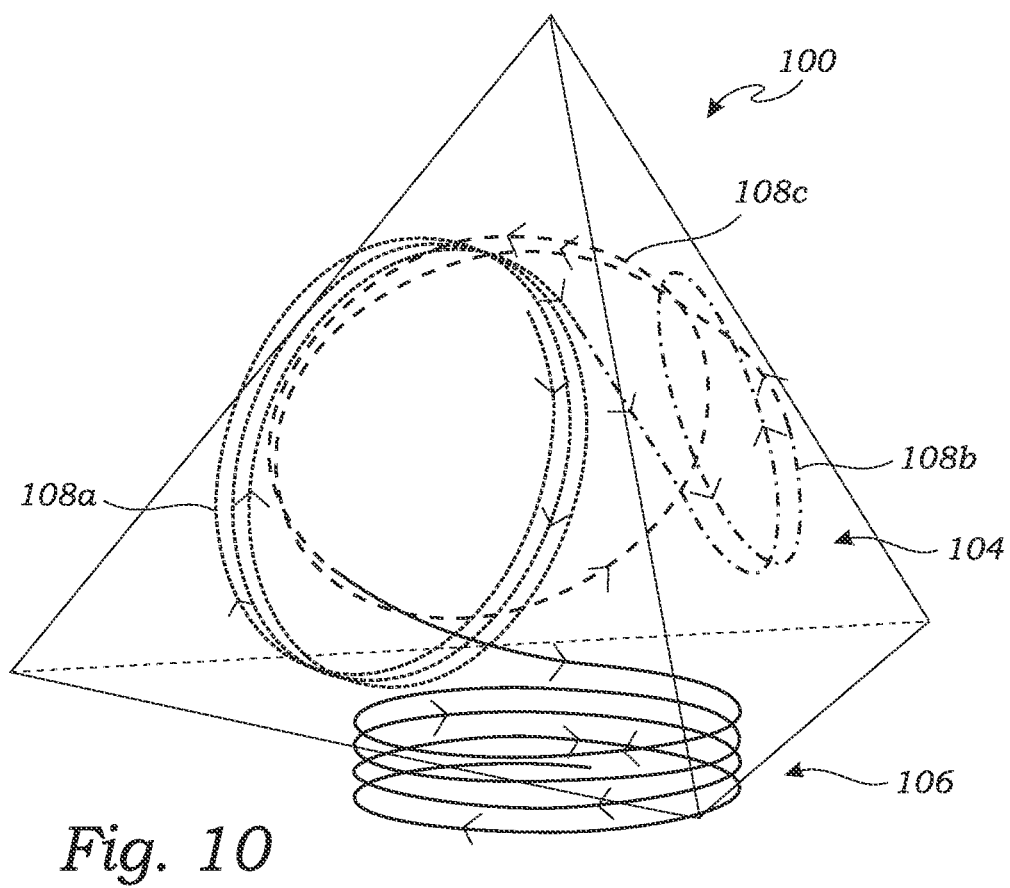
FIG. 10 is a side, perspective view of an example of an alternative pyramidal portion of the vaso-occlusive device of FIG. 6 in which the primary loops have varying diameters and varying numbers of turns.

In an alternative design of the vaso-occlusive device 100, the primary loops 108 may have differing diameters and/or differing numbers of turns of the wire 102, as illustrated in FIG. 9. As shown in FIG. 10, the first primary loop 108a has a larger diameter and more turns of the wire 102 (3 turns, i.e., 1080°) than the second primary loop 108b which has 1⅔ turns (600°). The third primary loop 108c also has a larger diameter than the second primary loop 108b (same diameter as the first primary loop 108a and 1⅔ turns (600°).

The distal primary loop 108a has a perimeter (i.e., length of the wire 102 forming the distal primary loop 108a) from its proximal end to its distal end. For a circular shaped distal primary loop 108a, the perimeter is a circumference or arc length equal to the $2\pi r(\Theta/360)$, where "r" is the radius of the arc, and "$\Theta$" is the angle of the arc. The individual turns of the distal primary loop 108a lie substantially in a respective one of a plurality of parallel planes, including a first plane, such that each loop lies in a substantially two-dimensional surface.

The primary portion 104 also includes a respective transition segment 110 of the wire 102 which is between and connecting each adjacent primary loop 108 to each other. Each transition segment 110 extends from the ending of one primary loop 108 to the beginning of the subsequent primary loop 108. Hence, the transition segment 110a extends from the proximal end (ending) of the primary loop 108a to the distal end (beginning) of the primary loop 108b, and the transition segment 110b extends from the proximal end (ending) of the primary loop 108b to the distal end (beginning) of the primary loop 108c. There is also a transition segment 112 from the proximal end of the last primary loop 108c winding to the distal end of the body portion 106, and a distal anchoring loop ("DAL") transition segment 111 from the proximal end of the distal anchoring loop 105 to the distal end of the first primary loop 108a.

Figure 11:
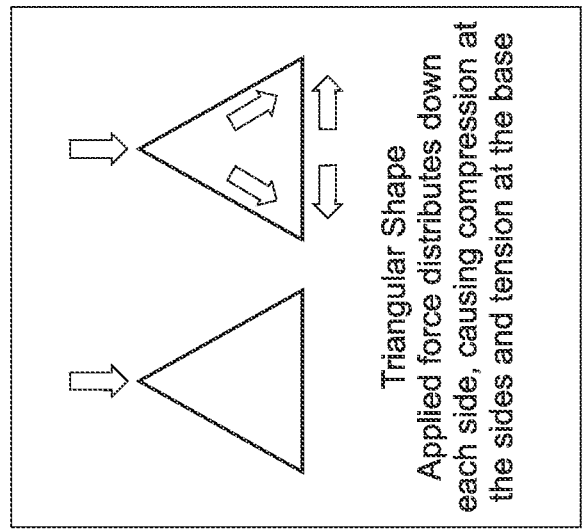
FIG. 11 depicts force and displacement diagrams for various shapes for a vaso-occlusive device.
Figure 11:
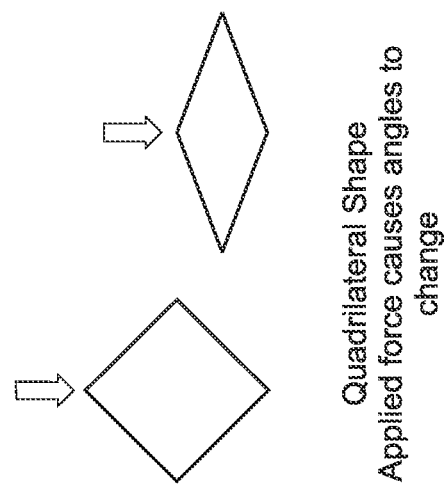
Figure 11:
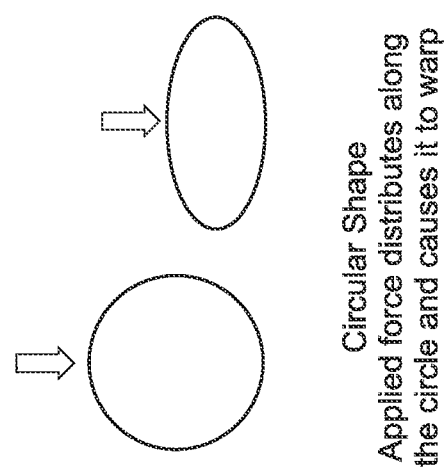

The distal anchoring loop 105 is at the distal-most end of the vaso-occlusive device 100 such that it is the first element of the vaso-occlusive device 100 to be inserted into a body cavity (e.g., an aneurysm) during deployment of vaso-occlusive device. The distal anchoring loop 105 has a substantially triangular shape and is substantially smaller in size than the first (i.e., distal) primary loop 108a. The distal anchoring loop 105 has a distal tip 107, which represents the leading tip of vaso-occlusive device 100, i.e., the distal tip 107 is the distal-most end of the vaso-occlusive device 100. The triangular shape of the distal anchoring loop 105 is more difficult to deform and/or displace upon deployment when it assumes its secondary configuration within an aneurysm than other shapes, such as circular and quadrilateral, as illustrated in FIG. 11.

Figure 12:
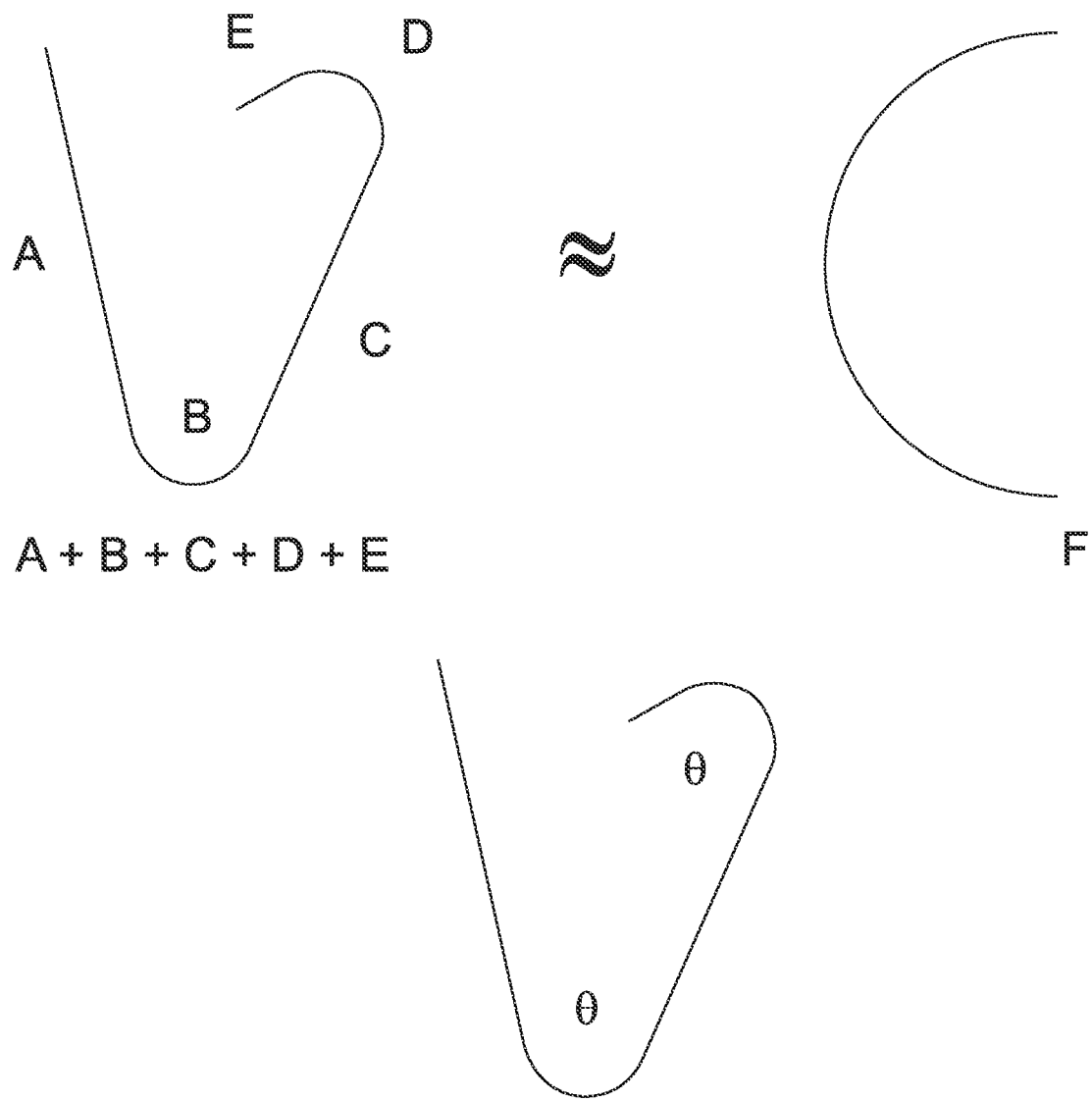
FIG. 12 is a diagram showing the geometry of a distal anchoring loop as disclosed herein.

As depicted in FIG. 12, the substantially triangular shape of the distal anchoring loop 105 is formed of a base "C" and two sides "E" and "A" connected to the base "C". Each of the sides "E" and "A" is connected to the base by rounded vertices, and the angle "$\Theta$" between the base "C" and each of the sides "E" and "A" is from 15° to 75°. Alternatively, the angle "Θ" between the base "C" and each of the sides "E" and "A" may be from 25° to 50°.

The distal anchoring loop 105 has an overall length which is the length of the wire 102 forming the distal anchoring loop 105. As shown in FIG. 12, overall length of the distal anchoring loop 105 illustrated in FIG. 6 is sum of the length of the 3 sides of the substantially triangular shape (A+C+E), and the length(s) of the arcs forming the filleted vertices (B+D) of the substantially triangular shape. As depicted in FIG. 12, the distal anchoring loop 105 may have an overall length "F" of 25% to 75% of the perimeter of the distal primary loop 108a, or the distal anchoring loop 105 may have an overall length of 40% to 60% of the perimeter of the distal primary loop 108a, or the distal anchoring loop 105 may have an overall length of less than 60% of the perimeter of the distal primary loop 108a.

Figure 13:
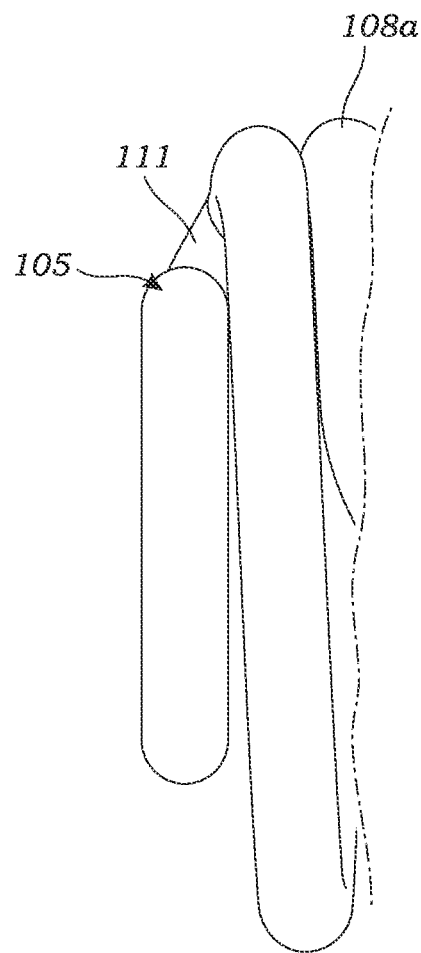
FIG. 13 is a side view of the distal anchoring loop and first primary loop of the vaso-occlusive device of FIG. 6.

As shown in FIG. 6, the distal anchoring loop 105 is positioned within a projection of the distal primary loop 108a. In other words, the distal anchoring loop 105 is positioned either within the perimeter of the distal primary loop 108a (e.g., co-planar), or it is positioned within a perpendicular projection of the perimeter of the distal primary loop 108a (e.g., the distal anchoring loop may be parallel to the first plane and out of the planes of distal primary loop 108a). The partial side view of FIG. 13 shows the distal anchoring loop 105 positioned out of, and parallel to, the planes of the distal primary loop 108a.

Figure 14B:
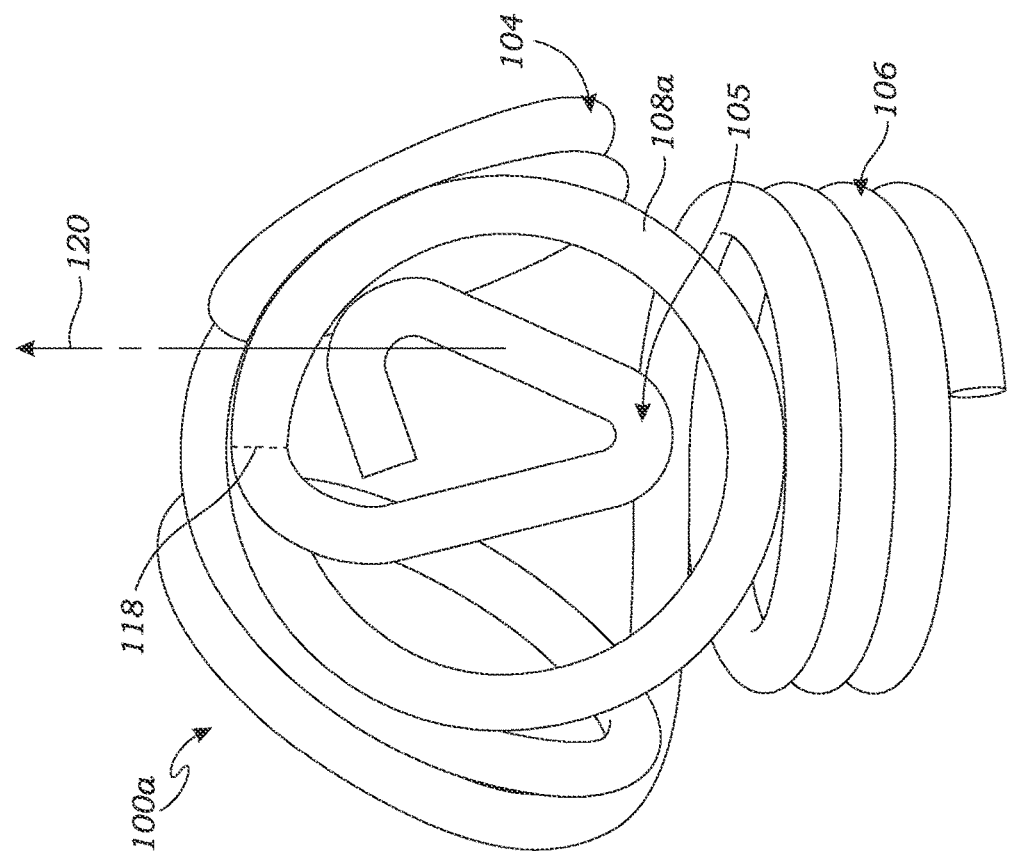
FIG. 14B is a side perspective view of an alternative design of the vaso-occlusive device of FIG. 6 having the position of the starting point of the distal anchoring loop at about a 12:00 o'clock position.
Figure 14A:
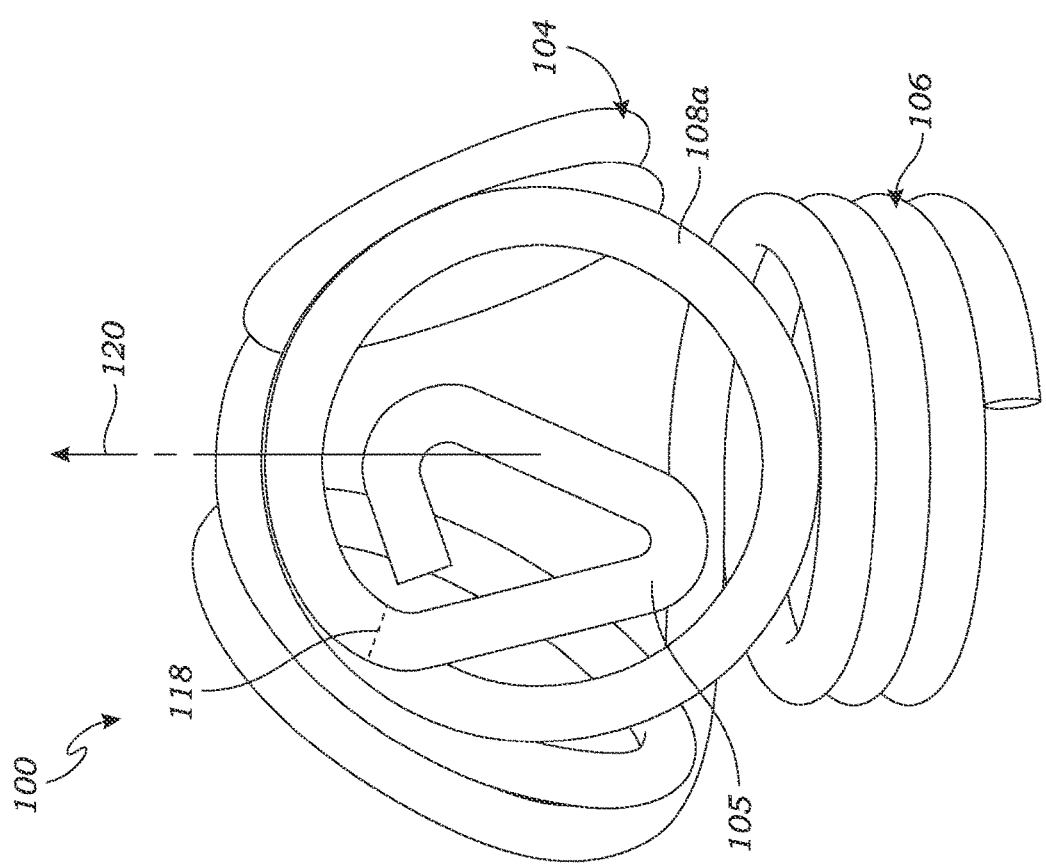
FIG. 14A is a side perspective view of the vaso-occlusive device of FIG. 6 illustrating the position of the starting point of the distal anchoring loop at about a 10:00 o'clock position.

FIGS. 14A and 14B illustrate a comparison of the vaso-occlusive device 100 having different locations for the starting point of the distal anchoring loop 105. The starting point of the distal anchoring loop 105 is where the distal anchoring loop 105 connects to the distal primary loop 108a. The vaso-occlusive device 100 in FIG. 14A has a starting point 118 of the distal anchoring loop 105 at between about a 10:00 o'clock and an 11:00 o'clock position relative to a longitudinal axis 120 of the primary configuration of the wire 102 being at a 12:00 o'clock position. This results in a distal primary loop 108a which starts at about this same position. This is in contrast to the vaso-occlusive device 100a in FIG. 14B which has a starting point 118 of the distal anchoring loop 105 at about a 12:00 o'clock position relative to the longitudinal axis 120. As a result of the different starting points of the distal anchoring loop 105, the distal primary loop 108a in the device 100 in FIG. 14A is longer than the distal primary loop 108a in the device 100a of FIG. 14B. This longer distal primary loop 108a of the vaso-occlusive device in FIG. 14A provides better initial framing of the device 100 during deployment of the vaso-occlusive device 100 into an aneurysm than the shorter distal primary loop 108a of the vaso-occlusive device in FIG. 14B. It has been found through empirical testing, the starting point 118 of the distal anchoring loop 105 between about a 10:00 o'clock and an 11:00 o'clock position relative to a longitudinal axis 120 provides better initial framing of the aneurysm during deployment than starting points 118 at other positions which provide different lengths for the distal primary loop 108a, such as between 12 o'clock to 3 o'clock, 3'clock to 6 o'clock, and 6 o'clock to 9 o'clock.

Referring to FIG. 6, the body portion 106 comprises a winding of the wire 102 which extends proximally from the primary portion 104. The body portion 106 may extend from the imaginary base of the pyramidal shape of the primary portion 104. In the illustrated example of FIG. 6, the body portion 106 is a helical coil extending proximally from the pyramidal portion 102. The body portion 106 may have a constant diameter, or alternatively, the body portion 106 may have a diameter which tapers outwardly or inwardly as it extends from the proximally from the primary portion 104. The body portion 106 comprises at least one full loop of the wire 102. The body portion 106 does not have a maximum degree of winding and may include any suitable number of turns, such as between 1 and 20 turns. The body portion 106 depicted in FIG. 6 has about 3-4 full turns of the wire 102.

Figure 15:
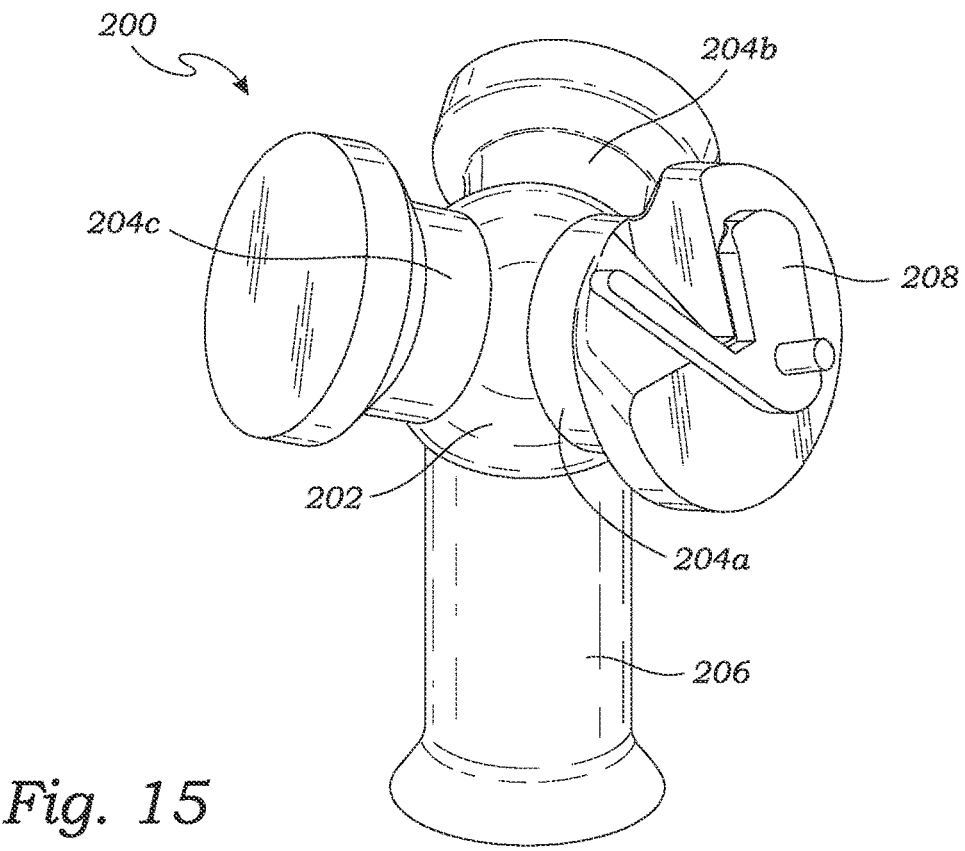
FIG. 15 is a side, perspective view of an exemplary mandrel for making the vaso-occlusive device of FIG. 6.

Turning to FIG. 15, an exemplary mandrel 200 for making the vaso-occlusive device 100 using a method 300 (described below) is illustrated. The mandrel 200 is used to wind the wire 102 around to form the secondary configuration of the vaso-occlusive device 100. The mandrel 200 is configured to form a vaso-occlusive device 100 comprising the primary portion 104 having a triangular pyramid shape, the distal anchoring loop 105 and base portion 106.

The mandrel 200 has a central, spherical element 202 (also referred to as a "support member"). A plurality of primary loop posts 204 extend outwardly from the central spherical element 202. Each primary loop post has a first end connected to the spherical element 202, a second end extended away from the spherical element 202, and a perimeter for winding the wire onto the respective primary loop post 204. The primary loop posts 204 are configured to form the primary loops 108 of the vaso-occlusive device 100. Accordingly, a primary loop post 204a forms the distal primary loop 108a, the primary loop post 204b forms the primary loop 108b and the primary loop post 204c forms the primary loop 108c, and so on depending on the number of primary loop post 204 and primary loops 108. The primary loop posts 204 are spaced angularly around the spherical element 202. In the depicted mandrel 200, the primary loop posts 204 are evenly spaced such that a respective longitudinal axis of each primary loop is evenly, angularly spaced around the spherical element 202. Accordingly, in the case of three primary loop posts 204, the primary loop posts 204 are spaced apart by 120°.

The perimeter of each primary loop post 204 has cross-sectional diameter which tapers outwardly as the primary loop post 204 extends away from the spherical element 202, as shown in FIG. 9 which shows a side view of one of the primary loop posts 204. The angle 114 of the taper of the primary loop posts 204 is the same as the taper of the primary loops 108, described herein. The longitudinal axis of each primary loop post 204 is also canted distally such that respective planes perpendicular to each respective longitudinal axis are non-parallel and non-perpendicular and the planes have an intersection which forms a pyramidal shape having an apex distal to the primary loop posts 204.

The mandrel 200 also has a distal anchoring loop sub-mandrel 208 coupled to the second end of the distal primary loop post 204a. The distal anchoring loop sub-mandrel 208 may extend outward from the second end of the distal primary loop post 204a. The distal anchoring loop sub-mandrel 208 is configured to form the distal anchoring loop 105 in its substantially triangular shaped loop from the wire 102. The distal anchoring loop sub-mandrel 208 is also oriented to set the starting point 118 of the distal anchoring loop 105 between about a 10:00 o'clock and an 11:00 o'clock position relative to a longitudinal axis 120.

The mandrel 200 also has a body post 206 extending from the spherical element 202. The body post 206 is configured to form the body portion 106 of the vaso-occlusive device 100. In the illustrated example of FIG. 15, the body post 206 extends proximally from the spherical element 202 and perpendicular to the base of the pyramidal shape of the primary portion 104. The body post 206 may be a cylinder having a constant diameter, or alternatively, the body post 206 may taper outwardly or inwardly as it extends from the spherical element 202.

Figure 16:
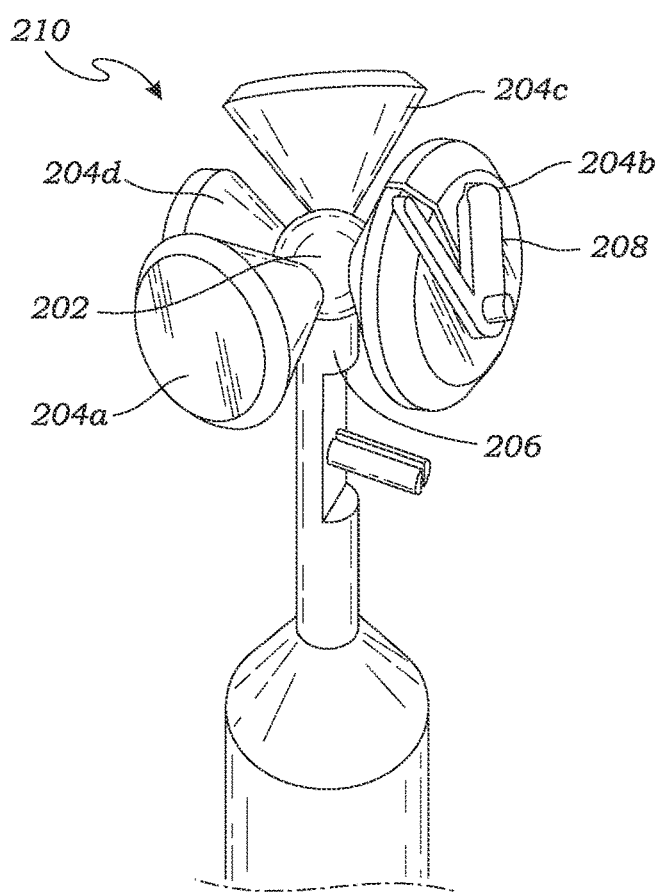
FIG. 16 is a side, perspective view of an exemplary mandrel for making a vaso-occlusive device having 4 distal coils forming the primary portion of a vaso-occlusive device having a shape of a square pyramid.

With the assistance of the present description, one of ordinary skill in the art would appreciate how to modify the mandrel 200 to be configured to make a vaso-occlusive device 100 comprising a primary portion 104 having the other pyramid shapes disclosed herein. For instance, FIG. 16 shows a mandrel 210 which is configured to make a vaso-occlusive device 100 comprising a primary portion 104 having a square pyramid shape. The mandrel 210 is same or substantially similar to the mandrel 200, except that the mandrel 210 has four primary loop posts 204 evenly, angularly spaced around the central, spherical member 202.

Figure 17A:
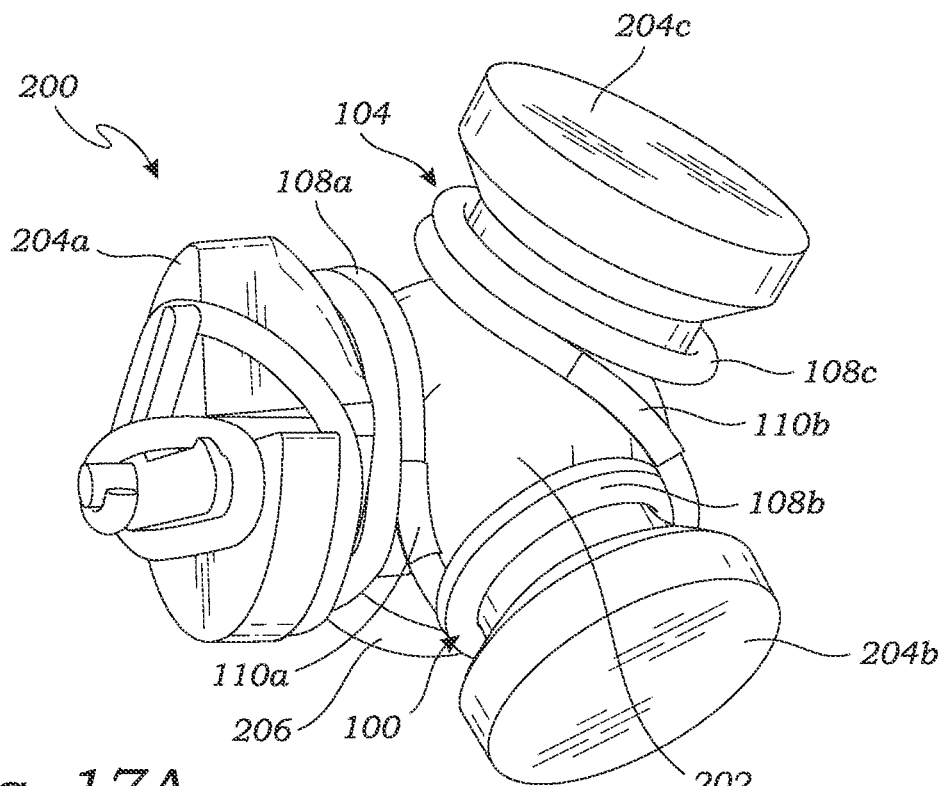
FIG. 17A is a top, perspective view of the mandrel of FIG. 15 with a wire wound around the mandrel to make the vaso-occlusive device of FIG. 6.
Figure 17B:
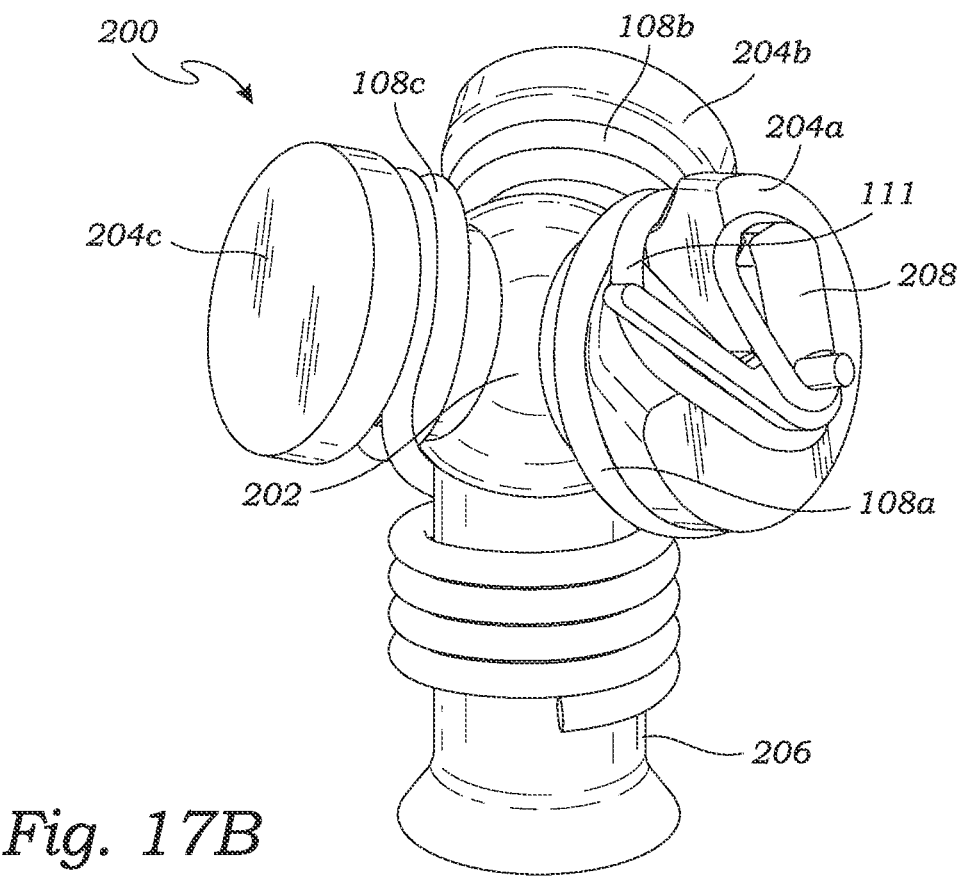
FIG. 17B is a side, perspective view of the mandrel of FIG. 17A with the wire wound around the mandrel to make the vaso-occlusive device of FIG. 6.
Figure 18:
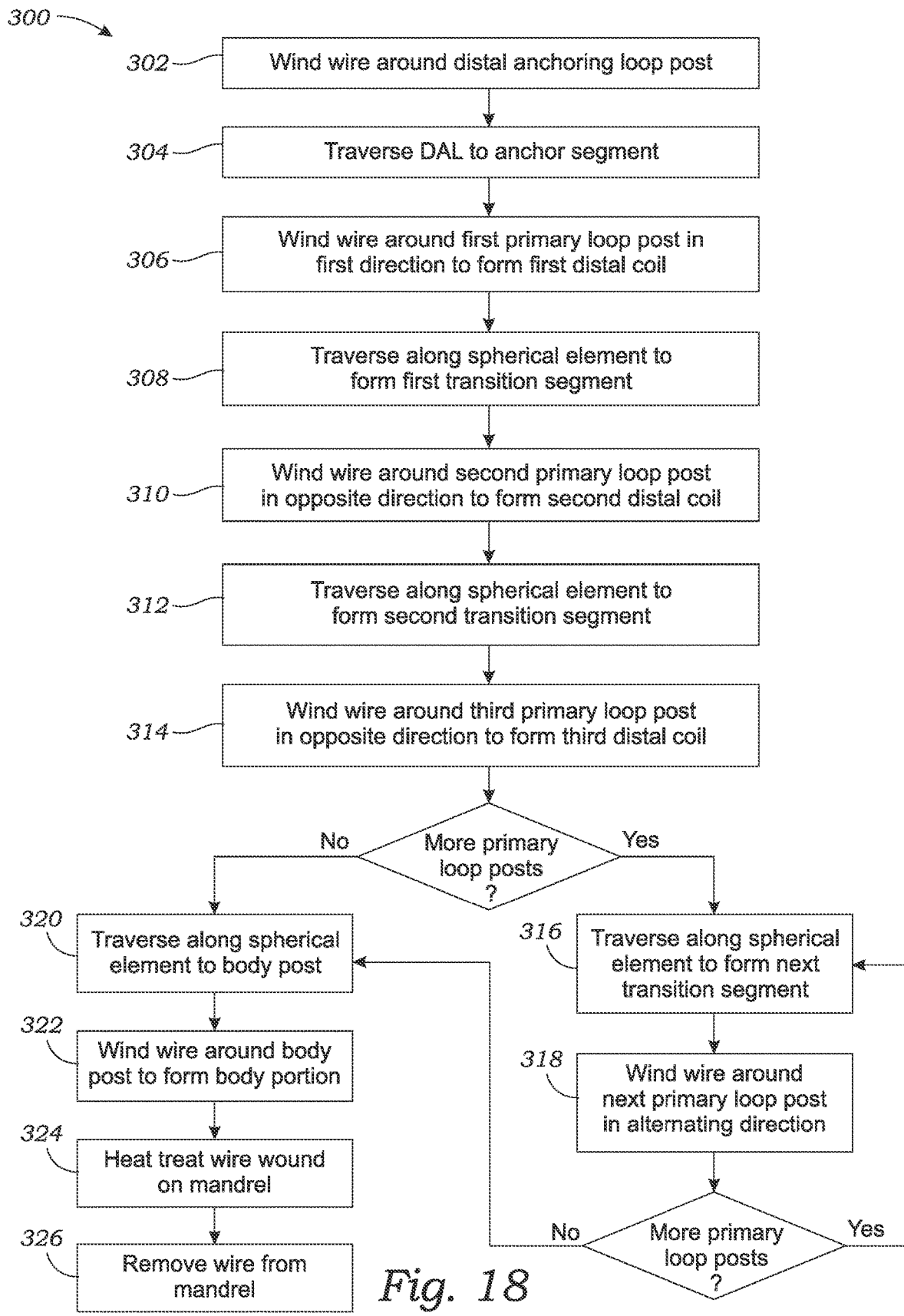
FIG. 18 is a flow chart showing a method of making the vaso-occlusive devices described herein using the mandrels described herein.

Turning to the illustrations in FIGS. 17A-17B and the flow chart of FIG. 18, an exemplary method 300 of making a vaso-occlusive device 100 using the mandrel 200 will now be described. A coil formed of a wire 102 having a primary configuration is wound around the mandrel 200. As described herein, the wire 102 may be formed of a shape memory material, and the primary configuration may be a configuration of the wire 102 in a constrained condition, such as within a sheath or delivery catheter. The primary configuration may have any suitable shape, such as a helical coil.

At step 302, the wire 102 is wound around the distal anchoring loop post 208 to form the distal anchoring loop 105. At step 304, the wire 302 is traversed to the distal end of the first primary loop 108a to form the DAL transition segment 111. At step 306, the wire 102 is wound around the first primary loop post 204a in a first direction and winding inward towards the intersection of the first primary loop post 204a and the spherical element 202. Subsequent windings start at the intersection of the post 204 and spherical element 202 and wind away from the spherical element 202. As used herein, a winding "direction" is relative to viewing inwardly along the winding axis toward the position of the attachment of a winding post to the central, spherical element or other central structure. Thus, the "first direction" as shown in the example of FIGS. 17 and 17B is a clockwise direction. The wire 102 is wound around the first primary loop post 204a to form the desired degree of winding for the first primary loop 108a, as described herein.

After winding the wire 102 around the first primary loop post 204a, at step 308, the wire 102 is traversed along the spherical element 202 forming the first transition segment 110a to the second primary loop post 204b immediately adjacent to the first primary loop 108a. At step 310, the wire 102 is wound around the second primary loop post 204b in a second direction opposite to the first direction (counterclockwise as shown in the example of FIGS. 16A-16B) starting at the intersection of the second primary loop post 204b and the spherical element 202. The wire 102 is wound around the second primary loop post 204b to form the desired degree of winding for the second primary loop 108a, as described herein.

After winding the wire 102 around the second primary loop post 204b, at step 312, the wire 102 is traversed along the spherical element 202 forming the second transition segment 110a to the third primary loop post 204c immediately adjacent to the second primary loop post 204b. At step 314, the wire 102 is wound around the third primary loop post 204c in a third direction opposite to the second direction (clockwise as shown in the example of FIGS. 16A-16B) starting at the intersection of the third primary loop post 204c and the spherical element 202. The wire 102 is wound around the third primary loop post 204c to form the desired degree of winding for the third primary loop 108c, as described herein.

Looking at a post 204 that is being wound axially along the axis of rotation, each of the three other posts 204 can be described at ⅓ rotations as the coil is being wound. Accordingly, a winding of 1⅔ loops or turns (i.e., 600°) means that as the wire 102 is wound around the post 204, each of the other posts 204, 206 that are passed represents and winding of ⅓ of a loop or turn. Hence, a winding of 1⅔ loops passes the three other posts 204, 206 once, and then re-passes 2 of the 3 other posts 204, 206 for a total of 1⅔ loops. A winding of about 2⅔ (960°) passes each of the other posts 204, 206 twice and then passes the next 2 posts a third time. The winding of a full loop (360°), or multiple full loops (360°×a whole number) plus another ⅔ of a loop, positions the end of a coil 108 to wind in the opposite direction on the next adjacent post 108. One of ordinary skill in the art will immediately understand how to determine the correct amount of loops for a mandrel having more than 3 posts 108, such as 4 posts 108, 5 posts 108, etc.

In the case of a mandrel 200 having more than 3 primary loop posts 204, at step 316, the wire is 102 traversed along the spherical element 202 in a next transition segment 110 to a next primary loop post 204 immediately adjacent to the preceding primary loop post 204. At step 318, the wire is wound around the next primary loop post 204 to form the next primary loop 108, and steps 316-318 are repeated for each additional primary loop post 204. After winding the wire 102 around the last of the primary loop posts 204, at step 320, the wire 102 is transitioned along the spherical element 202 to the body post 206. At step 322, the wire 102 is wound around the body post 206 to form the desired degree of winding for the body portion 106, as described herein.

At step 324, the wire 102 as wound on the mandrel 200 is heat treated to set the secondary configuration of the vaso-occlusive device 100 as wound on the mandrel 200. At step 326, the wire 102 is removed from the mandrel 200, and the wire 102 will take on the secondary configuration having the secondary shape as wound on the mandrel in its relaxed, unconstrained condition.

It is understood that the vaso-occlusive device 100 can also be formed by winding the wire 102 around the mandrel in the opposite direction. In other words, the wire 102 is first wound around the body post 206 to form the body portion 106. Then the wire 102 is wound around each of the primary loop posts 204 for greater than 360° to form each of the primary loops 108, and the resulting plurality of primary loops 108 are arranged in a pyramidal shape such that each primary loop 108 lies in a different lateral face of the pyramidal shape. The wire 102 is then wound around the distal anchoring loop post 208 post to form the distal anchoring loop 105. The wire 102 is also traversed to form each of the transition segments 110, in the opposite order from the method 300 described above. Indeed, the order of the steps of the method 300 may be performed in any suitable order, and the method 300 is not limited to any particular order of the steps.

Figure 19B:
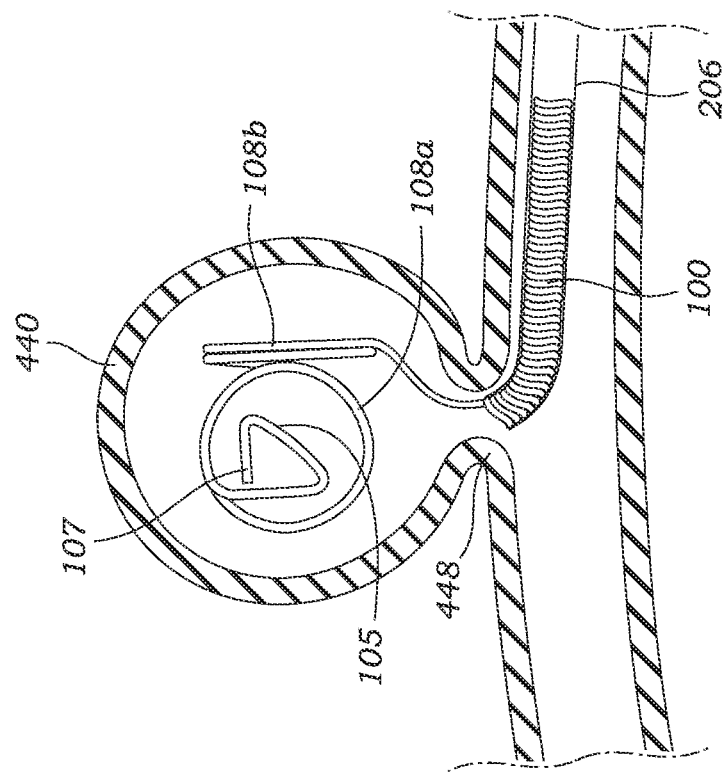
FIG. 19B is a cross-sectional side view of the vaso-occlusive device of FIG. 6 upon deployment of the distal anchoring loop and the first primary loop.
Figure 19A:
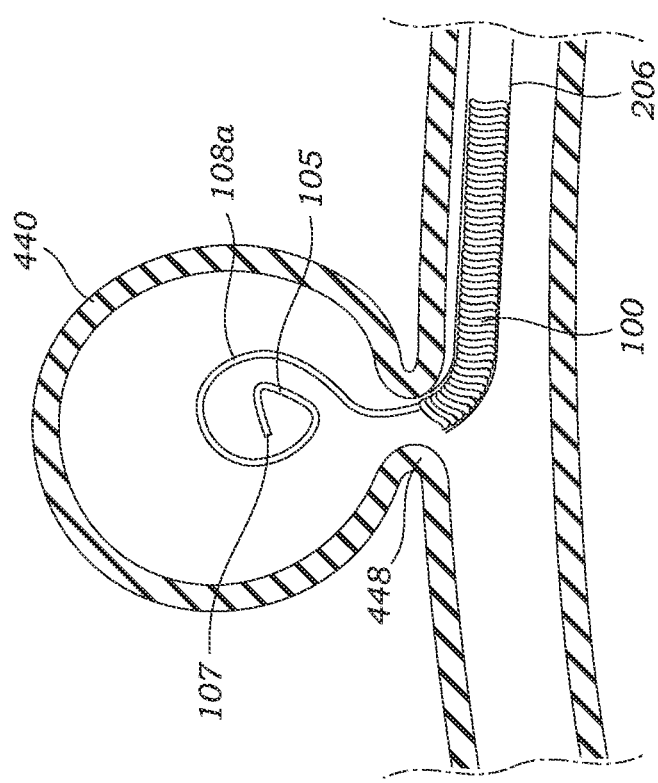
FIG. 19A is a cross-sectional side view of the initial deployment of the vaso-occlusive device of FIG. 6 with the distal anchoring loop inserted into the aneurysm.

Accordingly, disclosed herein are a vaso-occlusive device 100, and method 300 for making it, which alleviates the issues of herniation during placement and retention and provides effective framing of the aneurysm, while at the same time have a sufficiently soft and pliable structure that will not rupture the aneurysm, especially small and/or wide-necked aneurysms. The size, shape and location of the distal anchoring loop 105 effectively avoids herniation of the vaso-occlusive device 100 out of the aneurysm during deployment. FIGS. 19A and 19B illustrate the initial deployment of the vaso-occlusive device 100 out of a delivery catheter 206 into an aneurysm 440, showing how the distal anchoring loop 105 functions to avoid herniation during insertion. Upon initial deployment of the vaso-occlusive device 100, the distal tip 107 of the distal anchoring loop 105 first enters the aneurysm 440. As depicted in FIG. 19A, as the distal anchoring loop 105 is advanced out of the delivery catheter, it assumes its triangular shape in the secondary configuration of the vaso-occlusive device 100. As shown in FIG. 19B, as the vaso-occlusive device 100 continues to be advanced out of the delivery catheter 206, the distal anchoring loop 105 rotates and tumbles as the distal primary loop 108a enters the aneurysm and assumes its secondary configuration, while the distal tip 107 remains well within the aneurysm 440 and does not approach the neck 448 of the aneurysm 440, thereby minimizing the risk that the distal end 107 or any other part of the vaso-occlusive device 100 will herniate out of the aneurysm. The smaller distal anchoring loop 105 mitigates the risk of associated with an oversized distal primary loop 108a by providing a leading structure that is largely unaffected by variations in stiffness of the wire 102 and stiffening suture, if any. FIG. 19B also shows the distal primary loop 108a effectively framing the aneurysm 440 providing a sufficient stability to allow the remaining primary loops 108 and the base portion 106 to deploy and assume the secondary configuration of the vaso-occlusive device 100 within aneurysm with relative ease, and eliminating the need to a clinician to manipulate the delivery catheter 206 during deployment. This also removes the dependence on the skill of the clinician for a successful deployment.

Moreover, the pyramidal shape of the primary loops 108 of vaso-occlusive device 100 has an inherent ability to effectively dissipates forces applied to its apexes, thereby reducing the risk of imparting excessive forces on the walls of the aneurysm which could rupture the aneurysm, including small and/or wide-necked aneurysms. Furthermore, the primary loops are tapered to be inwardly facing and comprise full, closed loops and crossing, overlapping segments which fold more tightly than open loops when deployed in an aneurysm thereby reducing the risk of herniation during placement and retention. At the same time, shape stability is not compromised because of the inherent ability of the pyramidal shape to dissipate forces applied at the apexes. Furthermore, as illustrated in FIG. 6, the pyramidal shaped vaso-occlusive device 100 is more compact than a cube shaped vaso-occlusive device having 8 coils forming the 6 sides of a cube. In other words, the volume of the pyramidal shaped vaso-occlusive device 100 has a smaller volume than a cube. In addition, the primary loops 108 of the vaso-occlusive device 100 have a smaller diameter than the coils of a cube shaped vaso-occlusive device having the same or substantially same overall height as the vaso-occlusive device 100. This is because the diameter of each of the primary loops 108 is smaller than the overall height of the vaso-occlusive device 100 (e.g., 2.4 mm diameter of the primary loops vs. a 3.2 mm overall height of the vaso-occlusive device 100. Whereas the diameter of the coils of a cube shaped vaso-occlusive device extend the full height of the entire vaso-occlusive device (the height being the length of any one of the sides of the cube shaped vaso-occlusive device.

Figure 20B:
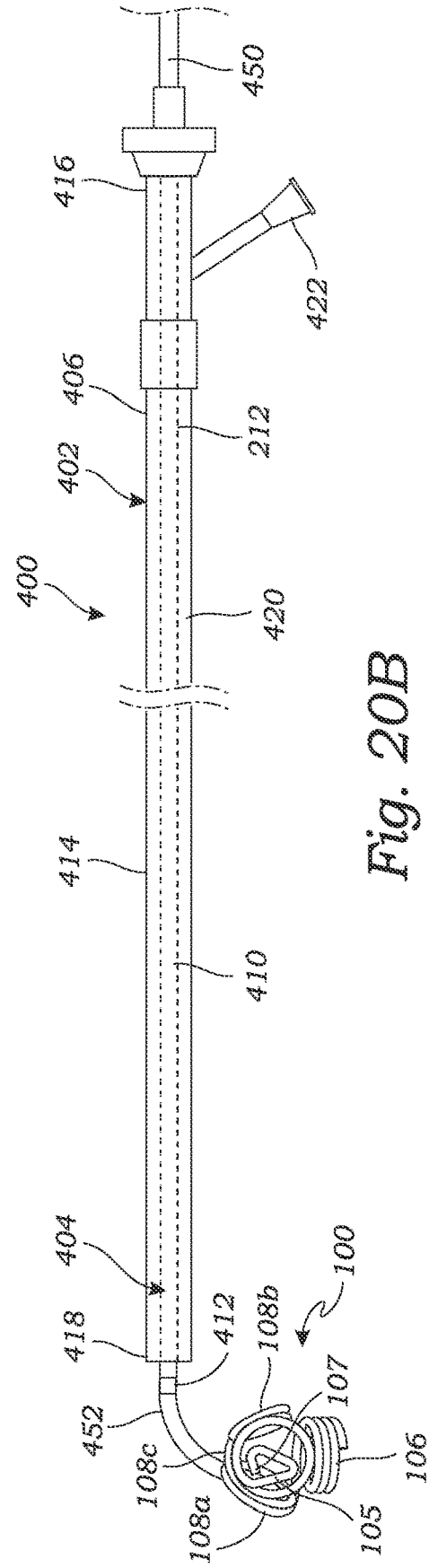
FIG. 20B is a cross-sectional, side view of the vaso-occlusive system of FIG. 20A with the vaso-occlusive device deployed out of the delivery catheter and in its expanded, deployed configuration.
Figure 21:
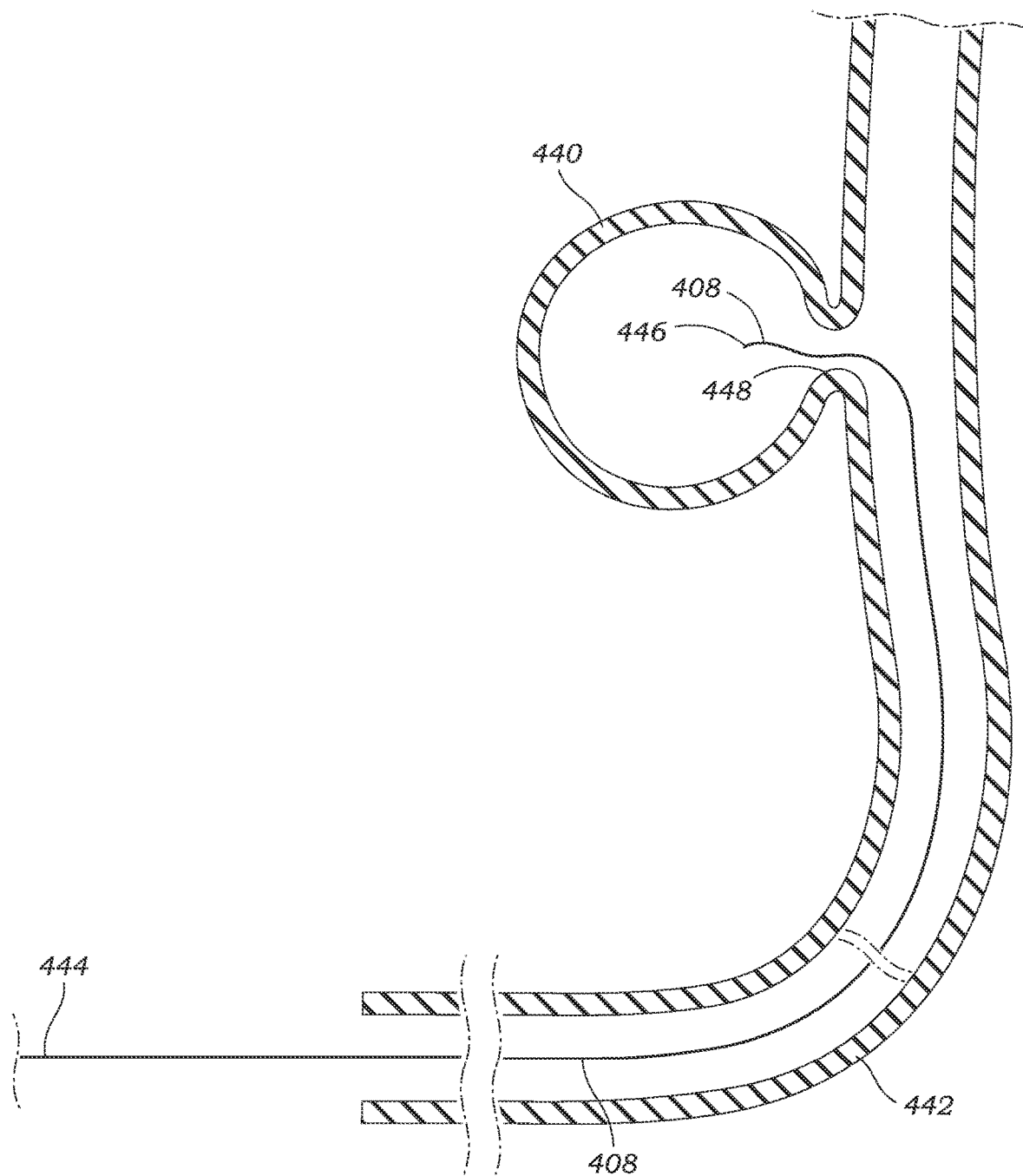
FIG. 21 a cross-sectional, side view depicting a guidewire advanced into a portion of a patient's vasculature to the location of an aneurysm.
Figure 22:
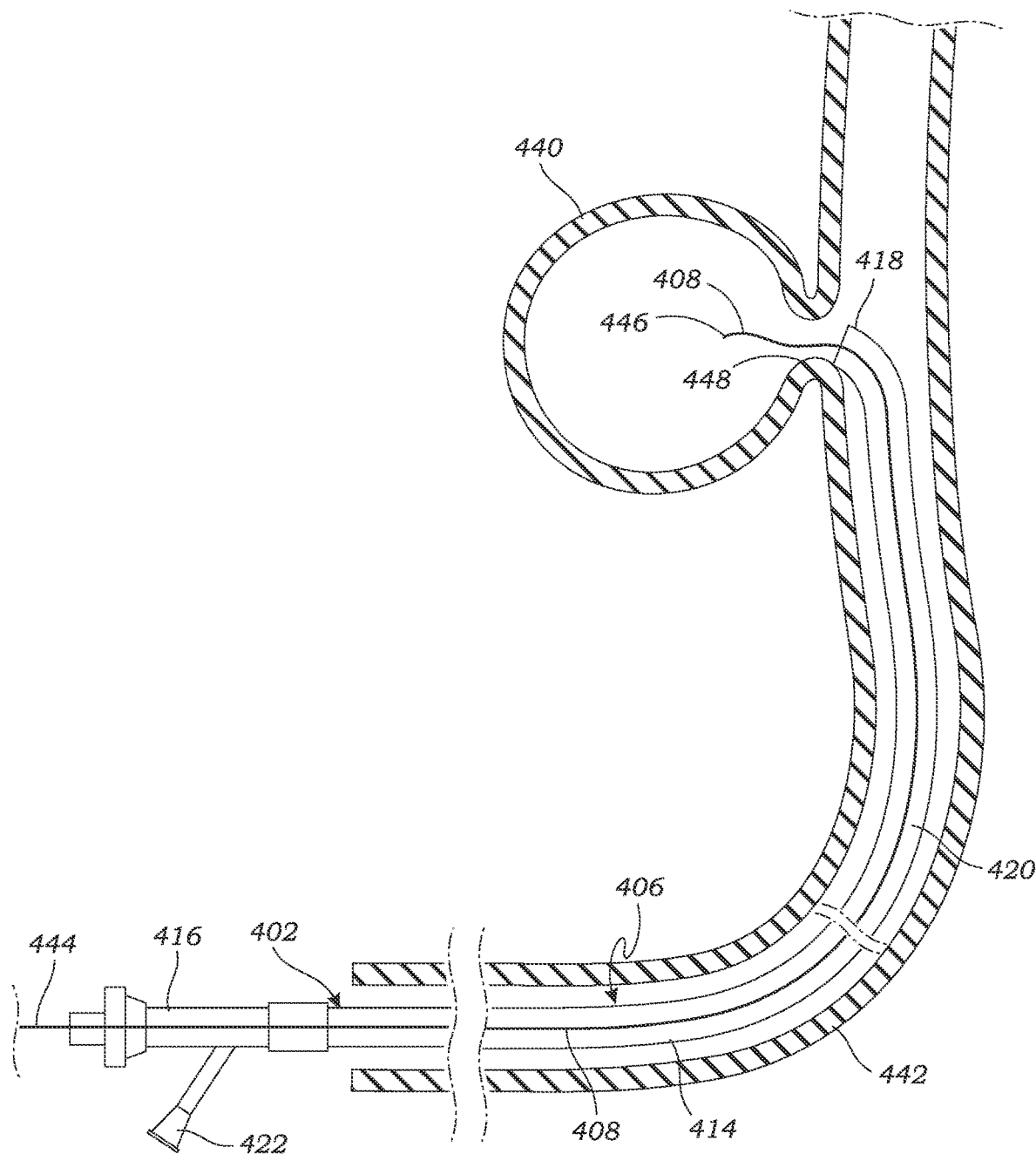
FIG. 22 is a cross-sectional, side view depicting the guidewire and patient's vasculature of FIG. 21 with a delivery catheter advanced over the guidewire.

Turning to FIGS. 20A and 20B, the vaso-occlusive device 100 may also be a component of a vaso-occlusive system 400 which can be used to deploy the vaso-occlusive device 100 into a body cavity, such as an aneurysm 440 (see FIGS. 21-24). The vaso-occlusive system 400 comprises a delivery assembly 402 and a vaso-occlusive assembly 404. As shown in FIGS. 21 and 22, the delivery assembly 402 may include a delivery catheter 406 and an optional guidewire 408. The vaso-occlusive assembly 404 comprises a vaso-occlusive device 100 and a pusher member 410 detachably coupled to the vaso-occlusive device 100 via a detachment device or junction 412. FIG. 20A shows the vaso-occlusive assembly 404 after it has been slidably disposed within the delivery catheter 406 such that the vaso-occlusive device 100 is in its compact, delivery configuration.

The delivery catheter 406 is typically an elongated, flexible tube, and can be, for example, a microcatheter or the like. The delivery catheter 406 comprises an elongate sheath body 414 having a proximal portion 416, a distal portion 418 and a lumen 420 extending from the proximal portion 416 to the distal portion 418. The proximal portion 416 of the delivery catheter 406 typically remains outside of the patient and accessible to the clinician when the vaso-occlusive system 400 is used, while the distal portion 418 is sized and dimensioned to reach remote locations of a patient's vasculature and is configured to deliver the vaso-occlusive device 100 to a body cavity such as an aneurysm. The delivery catheter 406 may also have one or more ports 422 in fluid communication with the lumen 420 for introducing into, or removing fluids from, the sheath body 414. The sheath body 414 may be composed of suitable polymeric materials, metals and/or alloys, such as polyethylene, stainless steel or other suitable biocompatible materials or combinations thereof. In some instances, the proximal portion 416 may include a reinforcement layer, such as a braided layer or coiled layer to enhance the pushability of the sheath body 414. The sheath body 414 may include a transition region between the proximal portion 416 and the distal portion 418.

The vaso-occlusive device 100 may be any of the vaso-occlusive device 100 disclosed herein, having any one or more of the features and aspects described herein.

The vaso-occlusive assembly 404 also comprises a pusher member 410. The pusher member 410 is configured to be slidably received within the lumen 420 of the delivery catheter 406. The pusher member 410 has a proximal portion 450, which typically extends proximal of the proximal portion 416 of the delivery catheter 406, and a distal portion 452 which is detachably coupled to the proximal end of the vaso-occlusive device 100 via the detachment device 412. The pusher member 410 may be a coil, wire, tendon, conventional guidewire, torqueable cable tube, hypotube, or the like, having a sufficient columnar strength to permit pushing of the vaso-occlusive device 100 out through distal end 418 of the delivery catheter 406 and into the aneurysmal sac 440 (see FIGS. 23 and 24).

The detachment device 412 provides a detachable connection between the pusher member 410 and the vaso-occlusive device 100. The detachment device 412 may comprise an electrolytically detachment, mechanical connector, heat activated detachment, dissolving detachment, or other mechanical, thermal and hydraulic mechanism. For instance, the detachment device 412 may be an electrolytically degradable segment for electrolytically decoupling the vaso-occlusive device 100 from the pusher member 410.

As shown in FIGS. 21 and 22, the optional guidewire 408 of the delivery assembly 402 has a proximal end 444 and a distal end 446. As shown in FIG. 22, after the guidewire 408 is positioned within the patient's vasculature 442 with the distal end 446 located at the target insertion site, the delivery catheter 406 is advanced over the guidewire 408 with the guidewire 408 disposed within the lumen 420 of the delivery catheter 406. In a "rapid-exchange" configuration of the delivery catheter 406 and guidewire 408, the guidewire 408 extends through only a distal portion of the delivery catheter 406, such as a rapid-exchange lumen. The guidewire 408 is typically used by first advancing the guidewire 408 through the patient's vasculature to the target insertion site (e.g., the neck 448 of an aneurysm to be filled by the vaso-occlusive device 100, see FIGS. 21-24), and then advancing the delivery catheter 406 over the guidewire 408 to the target insertion site.

Turning to FIGS. 21-25, an exemplary method 500 of using the vaso-occlusive system 200 to deploy the vaso-occlusive device 100 into an anatomical cavity will now be described. The method 500 will be described with respect to deploying the vaso-occlusive device 100 into an aneurysmal sac 440, as an example. However, the method 500 is not limited to deploying the vaso-occlusive device 100 into an aneurysmal sac 440, but may be used to deploy the vaso-occlusive device 100, or another medical device as disclosed herein, into any suitable anatomical cavity which is accessible via a patient's vasculature. Referring to the flow chart of FIG. 25 and FIG. 22, at step 502, the guidewire 408 is inserted into the patient's vasculature 442 and is advanced to the target insertion site, namely the aneurysmal sac 440. As described herein, the use of the guidewire 408 is optional, and is not required in the method 500 of using the vaso-occlusive system 200 to deploy the vaso-occlusive device 100.

Figure 23:
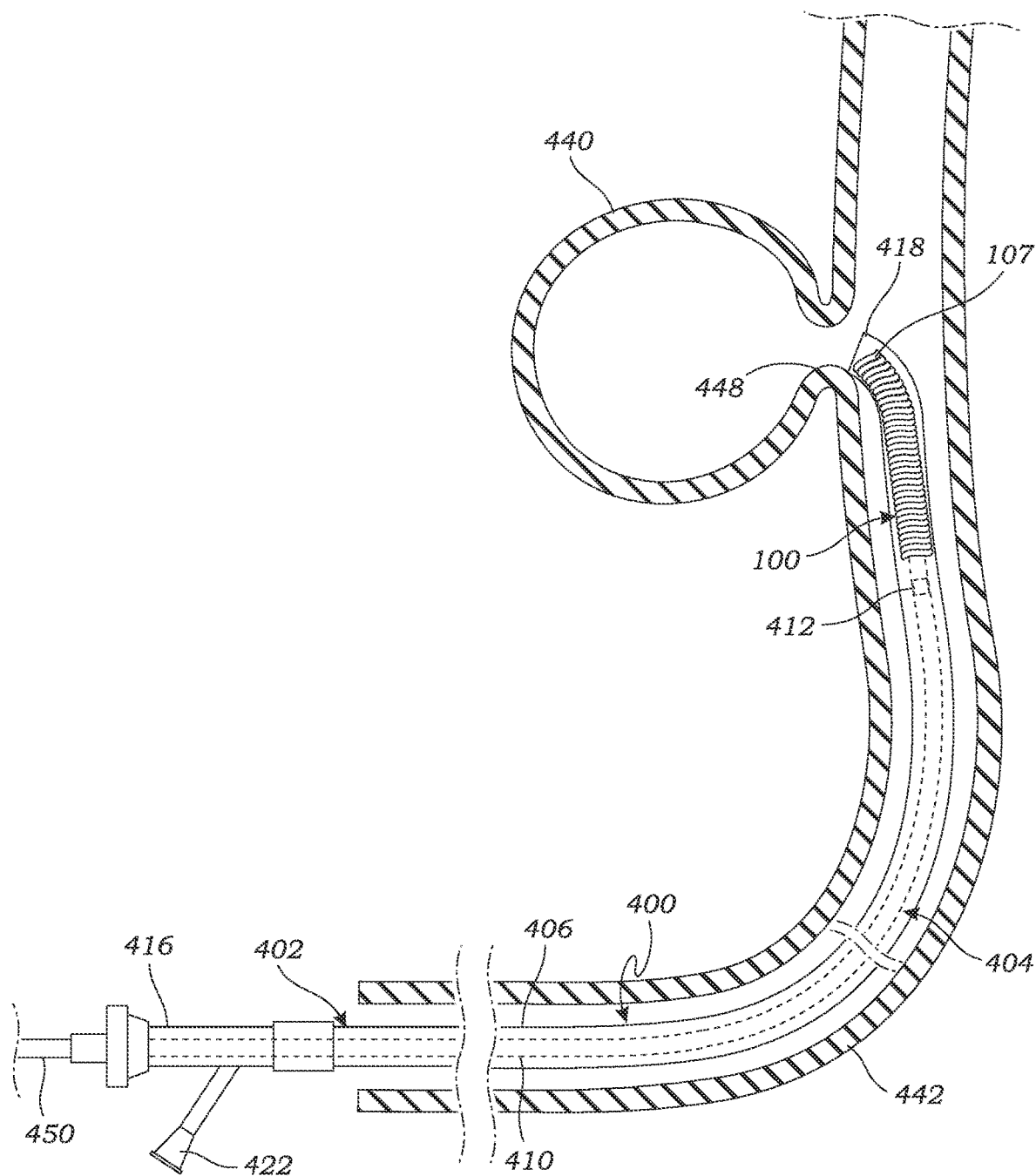
FIG. 23 is a cross-sectional, side view depicting the vaso-occlusive system of FIGS. 20A and 20B being advanced within the delivery catheter of FIG. 22 for deploying the vaso-occlusive device into the aneurysm.

At step 504, the delivery catheter 406 of the delivery assembly 402 is advanced over the guidewire 408 until it is positioned with the open distal end 418 adjacent or within the aneurysmal neck 448 of the aneurysm 440, as shown in FIG. 23. At step 506, the guidewire 408 is pulled out of the delivery catheter 406 leaving the delivery catheter 406 in position. At step 508, the vaso-occlusive assembly 404 is inserted into the delivery catheter 406 of the delivery assembly 402 and advanced within the delivery catheter 406 to position the distal end of the vaso-occlusive device 100 adjacent the distal portion 418 of the delivery catheter 406, as shown in FIG. 23. At this position, the proximal portion 450 of the pusher member 410 remains proximal and outside of the proximal portion 416 of the delivery catheter 406. Prior to inserting the vaso-occlusive device 100 into the delivery catheter 406, the vaso-occlusive device 100 may be pre-installed in a sheath such that the vaso-occlusive device 100 is in its constrained, delivery configuration (primary configuration). The vaso-occlusive device 100 is then inserted into the delivery catheter 406 by placing a distal end of the sheath in abutment with the proximal end 416 of the delivery catheter 406 and extruding the vaso-occlusive device 406 from the sheath into the delivery catheter 406 such that the vaso-occlusive device 100 remains in its delivery configuration within the delivery catheter 206.

Figure 24:
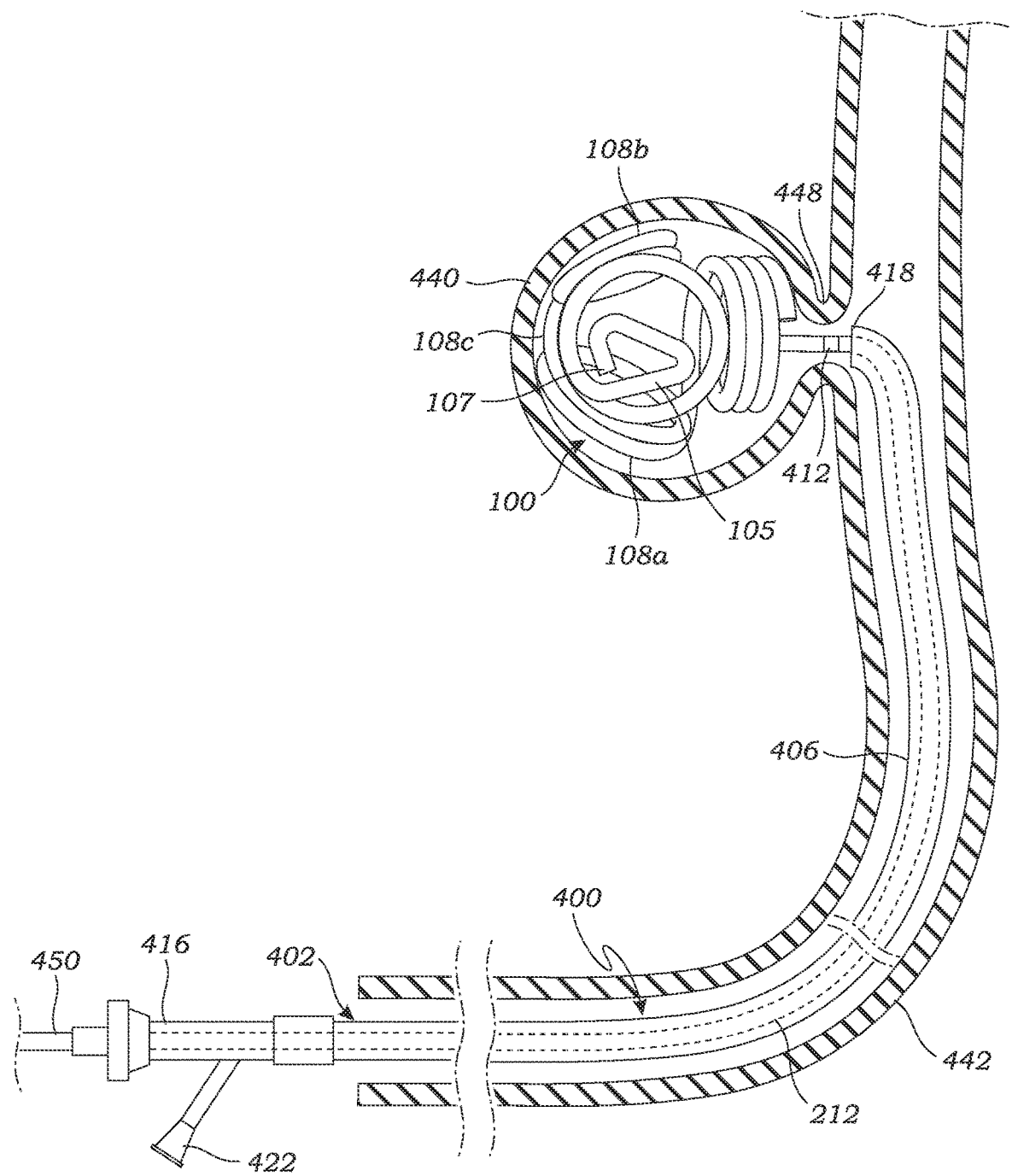
FIG. 24 is a cross-sectional, side view depicting the vaso-occlusive system of FIGS. 20A and 20B with the vaso-occlusive device deployed out of the delivery catheter shown in FIG. 22 and into the aneurysm.
Figure 25:
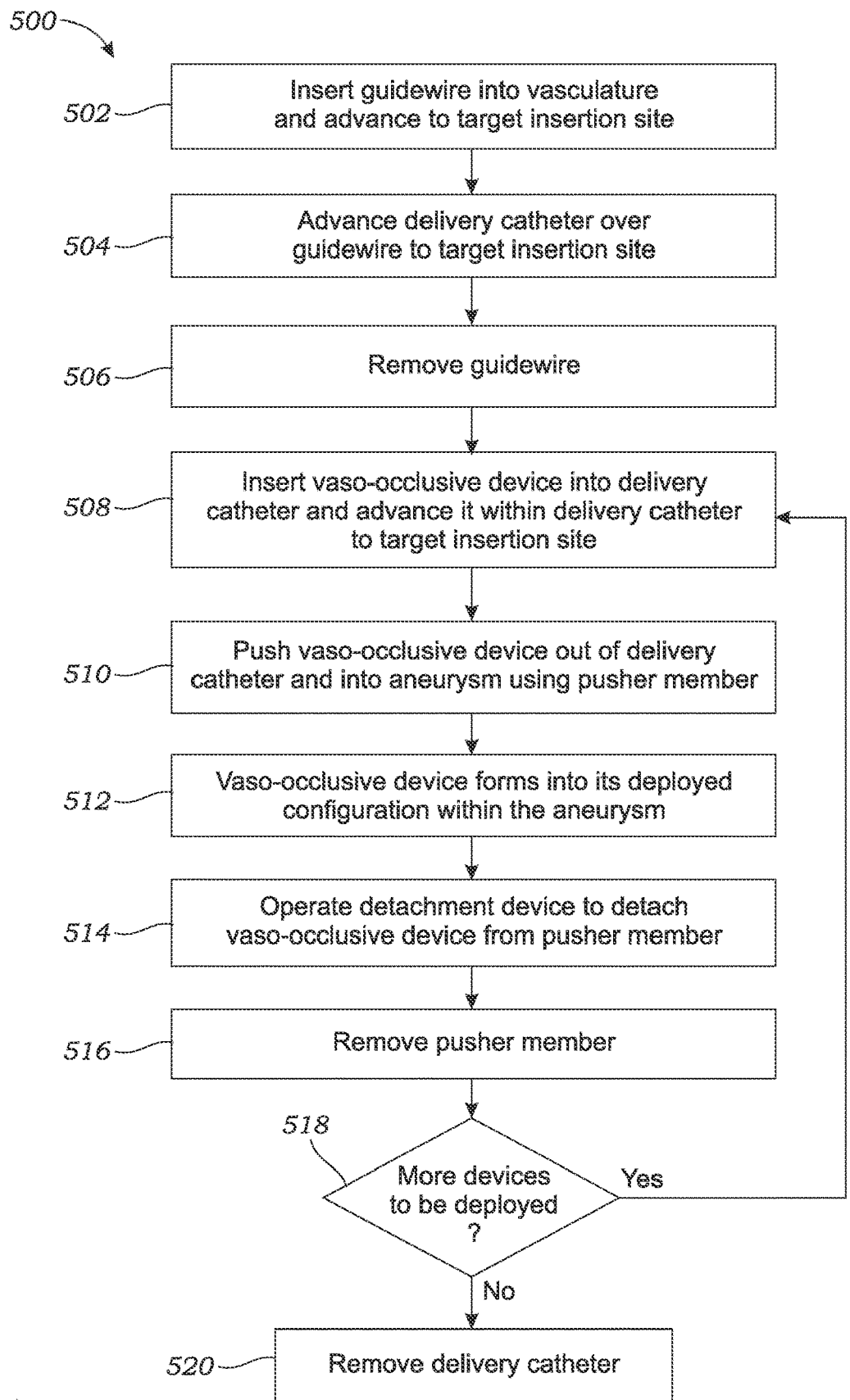
FIG. 25 is a flow chart of an exemplary method of using the vaso-occlusive system of FIGS. 20A and 20B to deploy the vaso-occlusive devices disclosed herein into an aneurysm.

At step 510, the vaso-occlusive device 100 is pushed through the lumen 420 of the delivery catheter 406 and distally out of the delivery catheter 406 by pushing on the proximal portion 450 of the pusher member 412. At step 512, as the vaso-occlusive device 100 is pushed out of the open distal end 418 of the delivery catheter 406, the primary portion 104 is advanced through the aneurysmal neck 448 and into the aneurysmal sac 440, the distal portion of the vaso-occlusive device 100 in its delivery configuration (primary configuration) expands into the secondary configuration (deployed configuration), and the primary loops 108 of the primary portion 104 are formed within the aneurysmal sac 440, as depicted in FIG. 24. Accordingly, the distal anchoring loop 105 is deployed into the aneurysmal sac 440 and assumes its triangular shape in the secondary configuration. Also at step 512, as the vaso-occlusive device 100 continues to be advanced out of the delivery catheter 406 via the pusher member 412, the primary loops 108 of the vaso-occlusive device 100 in their delivery configuration (primary configuration) expand into the secondary configuration (deployed configuration) forming the primary portion 104. Finally, the base portion 106 is inserted and assumes it secondary configuration within aneurysmal sac 440. Once the entire vaso-occlusive device 100 is inserted into the aneurysmal sac 440, at step 514, the detachment device 412 is actuated, activated or otherwise operated to detach the vaso-occlusive device 100 from the pusher-member 410. At step 516, the pusher member 410 is removed from the patient's vasculature 442 by withdrawing it out through the delivery catheter 406. If the single vaso-occlusive device 100 is sufficient to fill and occlude the aneurysm sac 440, then the method 500 proceeds to step 520 in which the delivery catheter 406 is removed from the patient's vasculature 442. If multiple vaso-occlusive devices 100 are being implanted, then the process of steps 508-516 are repeated to deliver a sufficient number of vaso-occlusive devices 100 to fill and occlude the aneurysmal sac 440. After the sufficient number of vaso-occlusive devices 100 are implanted in the aneurysmal sac 440, the delivery catheter 406 is removed at step 520.

Although particular embodiments of the disclosed inventions have been shown and described herein, it will be understood by those skilled in the art that they are not intended to limit the present inventions, and it will be obvious to those skilled in the art that various changes and modifications may be made (e.g., the dimensions of various parts) without departing from the scope of the disclosed inventions, which is to be defined only by the following claims and their equivalents. The specification and drawings are, accordingly, to be regarded in an illustrative rather than restrictive sense. The various embodiments of the disclosed inventions shown and described herein are intended to cover alternatives, modifications, and equivalents of the disclosed inventions, which may be included within the scope of the appended claims.

The invention claimed is:

1. A vaso-occlusive device, comprising:
    a coil formed of a wire having a primary configuration in a constrained condition, the primary configuration having a proximal end and a distal end;
    wherein the coil assumes a secondary configuration in a relaxed, unconstrained condition, the secondary configuration comprising:
    a primary portion comprising a plurality of primary loops, each of the primary loops comprising a winding of the wire forming a closed loop of greater than 360°, the primary loops including a distal primary loop which is a distal-most loop of the primary loops, the distal primary loop having a proximal end and a distal end and a perimeter length from the proximal end to the distal end, the distal primary loop having turns lying in a first plane and planes substantially parallel to said first plane; and
    a distal anchoring loop connected to the distal end of the distal primary loop, the distal anchoring loop having a substantially triangular shape, the distal anchoring loop having an overall length of 25% to 75% of the perimeter length of the distal primary loop, the distal anchoring loop positioned within a projection of the distal primary loop.

2. The vaso-occlusive device of claim 1, wherein the primary portion comprises a pyramidal portion formed from the primary loops, and the plurality of primary loops are arranged in a pyramidal shape such that each primary loop lies in a different lateral face of the pyramidal shape.

3. The vaso-occlusive device of claim 2, wherein each of the primary loops has a perimeter which tapers outwardly from an interior of the pyramidal portion, and each of the primary loops is connected to an adjacent primary loop(s) by a transition segment of the wire between each primary loop and the adjacent primary loop(s).

4. The vaso-occlusive device of claim 3, wherein the pyramidal shape is a tetrahedral forming a triangular pyramid shape having three lateral faces.

5. The vaso-occlusive device of claim 4, wherein the primary configuration comprises an elongate helical coil.

6. The vaso-occlusive device of claim 4, wherein the wire is formed from a shape memory material, and the secondary configuration is set by winding the wire on a mandrel and heat treating the wire wound on the mandrel.

7. The vaso-occlusive device of claim 4, wherein each of the primary loops has an average outer diameter in a range between 10 to 90 percent of a diameter of an aneurysm the vaso-occlusive device is designed to treat.

8. The vaso-occlusive device of claim 4, wherein each of the primary loops has an average outer diameter in a range between 55 to 85 percent of a diameter of an aneurysm the vaso-occlusive device is designed to treat.

9. The vaso-occlusive device of claim 3, wherein the pyramidal shape is a pentahedral forming a quadrilateral pyramid shape having four lateral faces.

10. The vaso-occlusive device of claim 3, wherein the pyramidal shape is a polyhedral shape formed of a polygonal base having n number of sides and n number of lateral faces connecting to an apex.

11. The vaso-occlusive device of claim 3, wherein each of the primary loops comprises at least 1 and ⅓ turns.

12. The vaso-occlusive device of claim 3, wherein the primary loops are overlapping in a transition from one primary loop to an adjacent primary loop.

13. The vaso-occlusive device of claim 2, wherein the secondary configuration further comprises a body portion proximal of the pyramidal portion, the body portion comprising a coil formed from the wire and extending proximally from the pyramidal portion.

14. The vaso-occlusive device of claim 1, wherein the substantially triangular shape of the distal anchoring loop is formed of a base and two sides connected to the base, wherein each of the sides is connected to the base by rounded vertices, and the angle between the base and each of the sides is from 15° to 75°.

15. The vaso-occlusive device of claim 1, wherein the substantially triangular shape of the distal anchoring loop is formed of a base and two sides connected to the base, wherein each of the sides is connected to the base by rounded vertices, and the angle between the base and each of the sides is from 25° to 50°.

16. The vaso-occlusive device of claim 1, wherein the overall length of the distal anchoring loop is from 40% to 60% of the perimeter length of the distal primary loop.

17. The vaso-occlusive device of claim 1, wherein a starting point of the distal anchoring loop where the distal anchoring loops connects to the distal primary loop is between a 10:00 o'clock position and an 11:00 o'clock position relative to a longitudinal axis of the primary configuration of the wire being at a 12:00 o'clock position.

18. The vaso-occlusive device of claim 1, wherein the distal anchoring loop is connected to the distal primary loop via a transition segment, and a starting point of the distal anchoring loop is where the distal anchoring loop connects to the transition segment.

19. The vaso-occlusive device of claim 1, wherein the distal anchoring loop lies out of the planes of the turns of the distal primary loop.

20. The vaso-occlusive device of claim 1, further comprising a second distal anchoring loop distal of the distal anchoring loop, the second distal anchoring loop having substantially the same shape and size as the distal anchoring loop and positioned parallel to the distal anchoring loop.

21. The vaso-occlusive device of claim 1, wherein the distal anchoring loop is positioned to the outside of the planes of the distal primary loop.

* * * * *